(12) United States Patent
Weston et al.

(10) Patent No.: US 10,576,148 B2
(45) Date of Patent: *Mar. 3, 2020

(54) USE OF VAP-1 INHIBITORS FOR TREATING FIBROTIC CONDITIONS

(71) Applicants: BIOTIE THERAPIES CORP., Turku (FI); THE UNIVERSITY OF BIRMINGHAM, Birmingham (GB)

(72) Inventors: Christopher Weston, Stourbridge (GB); Lee Charles Claridge, Kingswinford (GB); David Adams, Birmingham (GB); David Smith, Naantali (FI); Nina Westerlund, Turku (FI); Marjo Pihlavisto, Kaarina (FI); Thua Österman, Turku (FI)

(73) Assignees: BIOTIE THERAPIES CORP., Turku (FI); THE UNIVERSITY OF BIRMINGHAM, Birmingham (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/711,828

(22) Filed: Sep. 21, 2017

(65) Prior Publication Data

US 2018/0071388 A1 Mar. 15, 2018

Related U.S. Application Data

(63) Continuation of application No. 13/395,029, filed as application No. PCT/FI2010/050689 on Sep. 7, 2010, now Pat. No. 9,795,671.

(60) Provisional application No. 61/323,032, filed on Apr. 12, 2010, provisional application No. 61/240,402, filed on Sep. 8, 2009.

(51) Int. Cl.
| | | |
|---|---|---|
| *A61K 39/395* | (2006.01) | |
| *A61K 31/00* | (2006.01) | |
| *C07K 16/40* | (2006.01) | |
| *A61K 31/137* | (2006.01) | |
| *A61K 31/185* | (2006.01) | |
| *A61K 39/00* | (2006.01) | |
| *G01N 33/68* | (2006.01) | |
| *G01N 33/573* | (2006.01) | |

(52) U.S. Cl.
CPC .......... *A61K 39/3955* (2013.01); *A61K 31/00* (2013.01); *A61K 31/137* (2013.01); *A61K 31/185* (2013.01); *C07K 16/40* (2013.01); *G01N 33/573* (2013.01); *G01N 33/6893* (2013.01); *A61K 2039/505* (2013.01); *C07K 2317/76* (2013.01); *G01N 2333/90638* (2013.01); *G01N 2800/085* (2013.01)

(58) Field of Classification Search
None
See application file for complete search history.

(56) References Cited

U.S. PATENT DOCUMENTS

| | | |
|---|---|---|
| 2005/0032788 A1 | 2/2005 | Wagle et al. |
| 2007/0066646 A1 | 3/2007 | Clauzel et al. |
| 2008/0058922 A1 | 3/2008 | Stolen |
| 2013/0195883 A1 | 8/2013 | Weston et al. |

FOREIGN PATENT DOCUMENTS

| | | | |
|---|---|---|---|
| CN | 101087601 A | 12/2007 | |
| JP | 2004-501962 A | 1/2004 | |
| JP | 6290940 B2 | 3/2018 | |
| WO | WO 02/02090 A2 | 1/2002 | |
| WO | WO 02/38153 A1 | 5/2002 | |
| WO | WO 03/006003 A1 | 1/2003 | |
| WO | WO 03/093319 A1 | 11/2003 | |
| WO | WO 2004/067521 A1 | 8/2004 | |
| WO | WO 2004/087138 A1 | 10/2004 | |
| WO | WO 2005/014530 A2 | 2/2005 | |
| WO | WO 2005/072738 A1 | 8/2005 | |
| WO | WO 2005/080319 A1 | 9/2005 | |
| WO | WO 2005/082343 A2 | 9/2005 | |
| WO | WO 2005/089755 A1 | 9/2005 | |
| WO | WO 2006/011631 A2 | 2/2006 | |
| WO | WO 2006/013209 A2 | 2/2006 | |
| WO | WO 2006/028269 A2 | 3/2006 | |
| WO | WO 2006/094201 A2 | 9/2006 | |
| WO | WO 2007/005737 A2 | 1/2007 | |
| WO | WO 2008/129124 A1 | 10/2008 | |
| WO | WO-2008129124 A1 * | 10/2008 | ............. C07K 16/40 |
| WO | WO 2009/055002 A1 | 4/2009 | |
| WO | WO 2009/066152 A2 | 5/2009 | |
| WO | WO 2009/096609 A1 | 8/2009 | |
| WO | WO 2010/015870 A1 | 2/2010 | |

(Continued)

OTHER PUBLICATIONS

Hepar, "Hepatic Fibrogenesis-Inhibitory Action of MuIFN-β in Hepatic Fibrogenesis-Induced Model Caused by ConA Repetitive Administration," vol. 47, No. Suppl. 1, 2006, pp. A275, with partial English translation. ./.
Japanese Office Action, dated Dec. 11, 2018, for Japanese Application No. 2018-020789, with an English translation.
Merck, "Systemic Sclerosis—Musculoskeletal and Connective Tissue Disorders," Merck Manual, 18th Edition, Nov. 2005, 13 pages.
Boomsma et al., "Semicarbazide-sensitive amine oxidase (SSAO): from cell to circulation", Med Sci Monit, vol. 11, No. 4, 2005, pp. 122-126.
Chinese Office Action for Chinese Application No. 201080050348.1, dated Aug. 1, 2013 with English translation.

(Continued)

*Primary Examiner* — Vanessa L. Ford
*Assistant Examiner* — Sandra E Dillahunt
(74) *Attorney, Agent, or Firm* — Birch, Stewart, Kolasch & Birch, LLP

(57) ABSTRACT

The present invention relates to inhibitors of VAP-1 and their use as medicaments in treating fibrotic conditions. Furthermore, the present invention relates to a method of diagnosing a fibrotic condition on the basis of elevated level of soluble VAP-1 or SSAO activity in a bodily fluid, and to a kit for use in said diagnostic method.

17 Claims, 20 Drawing Sheets

Specification includes a Sequence Listing.

(56) References Cited

FOREIGN PATENT DOCUMENTS

| WO | WO 2010/031789 A1 | 3/2010 |
|---|---|---|
| WO | WO 2010/064020 A1 | 6/2010 |

OTHER PUBLICATIONS

Holt et al., "A Continuous Spectrophotometric Assay for Monoamine Oxidase and Related Enzymes in Tissue Homogenates," Analytical Biochemistry, vol. 244, Article No. AB969911, 1997, pp. 384-392.
International Preliminary Report on Patentability (Form PCT/IPEA/409), dated Dec. 13, 2011, for International Application No. PCT/FI2010/050689.
International Search Report (Form PCT/ISA/210), dated Jan. 20, 2011, for International Application No. PCT/FI2010/050689.
Ito et al., "A Clinical Evaluation of Serum Monoamine Oxidase, with Special Reference to Hepatic Fibrosis," Digestion, vol. 4, 1971, pp. 49-58.
Jaakkola et al., "Human Vascular Adhesion Protein-1 in Smooth Muscle Cells," American Journal of Pathology, vol. 155, No. 6, Dec. 1999, pp. 1953-1965.
Kurkijärvi et al., "Circulating Soluble Vascular Adhesion Protein 1 Accounts for the Increased Serum Monoamine Oxidase Activity in Chronic Liver Disease," Gastroenterology, vol. 119, No. 4, Oct. 2000, pp. 1096-1103.
Kurkijarvi et al., "Circulating Form of Human Vascular Adhesion Protein-1 (VAP-1): Increased Serum Levels in Inflammatory Liver Diseases", The Journal of Immunology, vol. 161, 1998, pp. 1549-1557.
Li et al., "Assay of plasma semicarbazide-sensitive amine oxidase and determination of its endogenous substrate methylamine by liquid chromatography," Journal of Chromatography B, vol. 810, 2004, pp. 277-282.
Lyles, "Mammalian Plasma and Tissue-bound Semicarbazide-sensitive Amine Oxidases: Biochemical, Pharmacologial and Toxicological Aspects," Int. J. Biochem. Cell Biol., vol. 28, No. 3, 1996, pp. 259-274.
Ma Lin et al., "Isoenzyme Composition of Human Plasma Monoamine Oxidase in Normal Subjects and in Fibrotic Liver Disease (39138)," Proceedings of the Society for Experimental Biology and Medicine, vol. 151, 1976, pp. 40-43.
McDonald et al., "Semicarbazide Sensitive Amine Oxidase and Vascular Adhesion Protein-1: One Protein Being Validated as a Therapeutic Target for Inflammatory Diseases," Annual Reports in Medicinal Chemistry, vol. 42, 2007, pp. 229-243.
McEwen, Jr. et al., "Abnormalities of serum monoamine oxidase in chronic liver disease," J. Lab. & Clin. Med., vol. 70, No. 1, Jul. 1967, pp. 36-47.
New Zealand Office Communication, dated Apr. 21, 2015, for New Zealand Application No. 706740.
New Zealand Office Communication, dated Nov. 10, 2014, for New Zealand Application No. 616432.
Palfreyman et al., "Haloallylamine inhibitors of MAO and SSAO and their therapeutic potential," J. Neural. Transm., vol. 41, Suppl., 1994, pp. 407-414.
Smith et al., "Cloning of Vascular Adhesion Protein 1 Reveals a Novel Multifunctional Adhesion Molecule," J. Exp. Med., vol. 188, No. 1, Jul. 6, 1998, pp. 17-27.
Written Opinion of the International Searching Authority (Form PCT/ISA/237), dated Jan. 20, 2011, for International Application No. PCT/FI2010/050689.
Zhou et al., "A One-Step Fluorometric Method for the Continuous Measurement of Monoamine Oxidase Activity," Analytical Biochemistry, vol. 253, Article AB972392, 1997, pp. 169-174.
Bonder et al., "Rules of Recruitment for Th1 and Th2 Lymphocytes in Inflamed Liver: A Rule for Alpha-4 Integrin and Vascular Adhesion Protein-1," Immunity, 2005, pp. 153-163, vol. 23, No. 2.
Brinckerhoff et al. Molecular Cloning of Human Synovial Cell Collagenase and Selection of a Single Gene from Genomic DNA. Journal of Clinical Investigation. 1987; 79:542-546.
Casset et al. A peptide mimetic of an anti-CD4 monoclonal antibody by rational design. Biochemical and Biophysical Research Communications, 2003; 307:198-205.
Japanese Office Action dated Sep. 24, 2014 for Japanese Application No. JP2012-528399.
Japanese Office Action dated Sep. 8, 2015 for Japanese Application No. JP2012-528399.
MacCallum et al. Antibody-antigen Interactions: Contact Analysis and Binding Site Topography. Journal of Molecular Biology, 262:732-745, 1996.
Paul. Fundamental Immunology, 3rd Edition, Raven Press, New York, Chapter 8, pp. 292-295, 1993.
Rosenbloom et al. Annals of Internal Medicine. 2010; 152:159-166.
Rosenbloom et al. Narrative review: Fibrotic diseases:cellular and molecular mechanisms and novel therapies. Annals of Internal Medicine. 2010; 152:159-166.
Salter-Cid et al. Anti-inflammtory effects of inhibiting the amine oxidase activty of semicarbazide-sensitive amine oxidase. The Journal of Pharmacology and Experimental Therapeutics. 2005; 315(2):553-562.
Vajdos et al. Comprehensive Functional Maps of the Antigen binding Site of an Anti-ErbB2 Antibody Obtained with Shotgun Scanning Mutagenesis. Journal of Molecular Biology, Jul. 5, 2002;320(2):415-28.
Wynn et al. Mechanism of fibrosis: therapeutic translation for fibrotic disease. Nature Medicine. 2012; 18(7):1028-1040.
Yu et al., "Involvement of Semicarbazide-Sensitive Amine Oxidase-Mediated Deamination in Atherogenesis in KKAy Diabetic Mice Fed with High Cholesterol Diet", Diabetologia, 2002, pp. 1255-1262, vol. 45.

* cited by examiner

SEQUENCE LISTING

```
<160> NUMBER OF SEQ ID NOS: 48

<210> SEQ ID NO 1
<211> LENGTH: 5
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: S, N or R
<220> FEATURE:
<221> NAME/KEY: MISC_FEATURE
<222> LOCATION: (2)..(2)
<223> OTHER INFORMATION: Y or S
<220> FEATURE:
<221> NAME/KEY: MISC_FEATURE
<222> LOCATION: (3)..(3)
<223> OTHER INFORMATION: A, G or W
<220> FEATURE:
<221> NAME/KEY: MISC_FEATURE
<222> LOCATION: (4)..(4)
<223> OTHER INFORMATION: M or I
<220> FEATURE:
<221> NAME/KEY: MISC_FEATURE
<222> LOCATION: (5)..(5)
<223> OTHER INFORMATION: H or S

<400> SEQUENCE: 1

Xaa Xaa Xaa Xaa Xaa
1               5

<210> SEQ ID NO 2
<211> LENGTH: 17
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: V, A or N
<220> FEATURE:
<221> NAME/KEY: MISC_FEATURE
<222> LOCATION: (2)..(2)
<223> OTHER INFORMATION: I or L
<220> FEATURE:
<221> NAME/KEY: MISC_FEATURE
<222> LOCATION: (3)..(3)
<223> OTHER INFORMATION: W, G or K
<220> FEATURE:
<221> NAME/KEY: MISC_FEATURE
<222> LOCATION: (4)..(4)
<223> OTHER INFORMATION: F, Q, V or Y
```

```
<220> FEATURE:
<221> NAME/KEY: MISC_FEATURE
<222> LOCATION: (5)..(5)
<223> OTHER INFORMATION: D or G
<220> FEATURE:
<221> NAME/KEY: MISC_FEATURE
<222> LOCATION: (7)..(7)
<223> OTHER INFORMATION: S, G or I
<220> FEATURE:
<221> NAME/KEY: MISC_FEATURE
<222> LOCATION: (8)..(8)
<223> OTHER INFORMATION: N, E, Y or no amino acid
<220> FEATURE:
<221> NAME/KEY: MISC_FEATURE
<222> LOCATION: (9)..(9)
<223> OTHER INFORMATION: E, K or T
<220> FEATURE:
<221> NAME/KEY: MISC_FEATURE
<222> LOCATION: (10)..(10)
<223> OTHER INFORMATION: Y, D or N
<220> FEATURE:
<221> NAME/KEY: MISC_FEATURE
<222> LOCATION: (11)..(11)
<223> OTHER INFORMATION: Y or H
<220> FEATURE:
<221> NAME/KEY: MISC_FEATURE
<222> LOCATION: (12)..(12)
<223> OTHER INFORMATION: V or A
<220> FEATURE:
<221> NAME/KEY: MISC_FEATURE
<222> LOCATION: (16)..(16)
<223> OTHER INFORMATION: K or R

<400> SEQUENCE: 2

Xaa Xaa Xaa Xaa Xaa Gly Xaa Xaa Xaa Xaa Xaa Xaa Asp Ser Val Xaa
1               5                   10                  15
Gly

<210> SEQ ID NO 3
<211> LENGTH: 14
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: D or E
<220> FEATURE:
<221> NAME/KEY: MISC_FEATURE
<222> LOCATION: (2)..(2)
<223> OTHER INFORMATION: A, G, K, P or Y
<220> FEATURE:
<221> NAME/KEY: MISC_FEATURE
<222> LOCATION: (3)..(3)
<223> OTHER INFORMATION: W, F, G or N
<220> FEATURE:
<221> NAME/KEY: MISC_FEATURE
<222> LOCATION: (4)..(4)
<223> OTHER INFORMATION: F, G or no amino acid
<220> FEATURE:
<221> NAME/KEY: MISC_FEATURE
<222> LOCATION: (5)..(5)
<223> OTHER INFORMATION: G, S or no amino acid
<220> FEATURE:
<221> NAME/KEY: MISC_FEATURE
<222> LOCATION: (6)..(6)
<223> OTHER INFORMATION: G or no amino acid
<220> FEATURE:
<221> NAME/KEY: MISC_FEATURE
<222> LOCATION: (7)..(7)
<223> OTHER INFORMATION: T or no amino acid
<220> FEATURE:
<221> NAME/KEY: MISC_FEATURE
<222> LOCATION: (8)..(8)
<223> OTHER INFORMATION: Y or no amino acid
<220> FEATURE:
<221> NAME/KEY: MISC_FEATURE
```

```
<222> LOCATION: (9)..(9)
<223> OTHER INFORMATION: E, F or no amino acid
<220> FEATURE:
<221> NAME/KEY: MISC_FEATURE
<222> LOCATION: (10)..(10)
<223> OTHER INFORMATION: F, G, S, V or W
<220> FEATURE:
<221> NAME/KEY: MISC_FEATURE
<222> LOCATION: (11)..(11)
<223> OTHER INFORMATION: Y or G
<220> FEATURE:
<221> NAME/KEY: MISC_FEATURE
<222> LOCATION: (12)..(12)
<223> OTHER INFORMATION: F or I

<400> SEQUENCE: 3

Xaa Xaa Xaa Xaa Xaa Xaa Xaa Xaa Xaa Xaa Xaa Xaa Asp Tyr
1               5                   10

<210> SEQ ID NO 4
<211> LENGTH: 5
<212> TYPE: PRT
<213> ORGANISM: Homo sapiens

<400> SEQUENCE: 4

Ser Tyr Ala Met His
1               5

<210> SEQ ID NO 5
<211> LENGTH: 5
<212> TYPE: PRT
<213> ORGANISM: Homo sapiens

<400> SEQUENCE: 5

Asn Tyr Trp Met Ser
1               5

<210> SEQ ID NO 6
<211> LENGTH: 5
<212> TYPE: PRT
<213> ORGANISM: Homo sapiens

<400> SEQUENCE: 6

Ser Tyr Ala Met His
1               5

<210> SEQ ID NO 7
<211> LENGTH: 5
<212> TYPE: PRT
<213> ORGANISM: Homo sapiens

<400> SEQUENCE: 7

Arg Ser Gly Ile His
1               5

<210> SEQ ID NO 8
<211> LENGTH: 5
<212> TYPE: PRT
<213> ORGANISM: Homo sapiens

<400> SEQUENCE: 8

Ser Tyr Gly Met His
1               5

<210> SEQ ID NO 9
<211> LENGTH: 17
<212> TYPE: PRT
```

```
<213> ORGANISM: Homo sapiens

<400> SEQUENCE: 9

Val Ile Trp Phe Asp Gly Ser Asn Glu Asn Tyr Val Asp Ser Val Lys
1               5                   10                  15

Gly

<210> SEQ ID NO 10
<211> LENGTH: 17
<212> TYPE: PRT
<213> ORGANISM: Homo sapiens

<400> SEQUENCE: 10

Asn Ile Lys Gln Asp Gly Ser Glu Lys Tyr Tyr Val Asp Ser Val Arg
1               5                   10                  15

Gly

<210> SEQ ID NO 11
<211> LENGTH: 17
<212> TYPE: PRT
<213> ORGANISM: Homo sapiens

<400> SEQUENCE: 11

Val Leu Trp Phe Asp Gly Ser Asn Glu Asp Tyr Ala Asp Ser Val Lys
1               5                   10                  15

Gly

<210> SEQ ID NO 12
<211> LENGTH: 17
<212> TYPE: PRT
<213> ORGANISM: Homo sapiens

<400> SEQUENCE: 12

Val Ile Trp Tyr Asp Gly Ile Tyr Lys Tyr Tyr Ala Asp Ser Val Lys
1               5                   10                  15

Gly

<210> SEQ ID NO 13
<211> LENGTH: 16
<212> TYPE: PRT
<213> ORGANISM: Homo sapiens

<400> SEQUENCE: 13

Ala Ile Gly Val Gly Gly Gly Thr Tyr His Val Asp Ser Val Lys Gly
1               5                   10                  15

<210> SEQ ID NO 14
<211> LENGTH: 8
<212> TYPE: PRT
<213> ORGANISM: Homo sapiens

<400> SEQUENCE: 14

Asp Ala Trp Ser Tyr Phe Asp Tyr
1               5

<210> SEQ ID NO 15
<211> LENGTH: 14
<212> TYPE: PRT
<213> ORGANISM: Homo sapiens

<400> SEQUENCE: 15

Asp Tyr Phe Gly Ser Gly Thr Tyr Phe Phe Tyr Phe Asp Tyr
```

```
1               5                    10

<210> SEQ ID NO 16
<211> LENGTH: 8
<212> TYPE: PRT
<213> ORGANISM: Homo sapiens

<400> SEQUENCE: 16

Asp Gly Trp Gly Tyr Phe Asp Tyr
1               5

<210> SEQ ID NO 17
<211> LENGTH: 8
<212> TYPE: PRT
<213> ORGANISM: Homo sapiens

<400> SEQUENCE: 17

Glu Lys Asn Trp Gly Ile Asp Tyr
1               5

<210> SEQ ID NO 18
<211> LENGTH: 11
<212> TYPE: PRT
<213> ORGANISM: Homo sapiens

<400> SEQUENCE: 18

Asp Pro Gly Phe Gly Glu Val Tyr Phe Asp Tyr
1               5                    10

<210> SEQ ID NO 19
<211> LENGTH: 117
<212> TYPE: PRT
<213> ORGANISM: Homo sapiens

<400> SEQUENCE: 19

Gln Val Gln Leu Val Glu Ser Gly Gly Val Val Gln Pro Gly Arg
1               5                    10                  15

Ser Leu Arg Leu Ser Cys Ala Ala Ser Gly Phe Thr Phe Ser Tyr
                20                  25                  30

Ala Met His Trp Val Arg Gln Thr Pro Gly Lys Gly Leu Glu Trp Val
            35                  40                  45

Ala Val Ile Trp Phe Asp Gly Ser Asn Glu Asn Tyr Val Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Thr Leu Arg Ala Glu Asp Thr Ala Val Tyr Tyr Cys
                85                  90                  95

Ala Arg Asp Ala Trp Ser Tyr Phe Asp Tyr Trp Gly Gln Gly Thr Leu
            100                 105                 110

Val Thr Val Ser Ser
        115

<210> SEQ ID NO 20
<211> LENGTH: 123
<212> TYPE: PRT
<213> ORGANISM: Homo sapiens

<400> SEQUENCE: 20

Glu Val Gln Leu Val Glu Ser Gly Gly Gly Leu Val Gln Pro Gly Gly
1               5                    10                  15

Ser Leu Arg Leu Ser Cys Ala Ala Ser Gly Phe Ile Phe Ser Asn Tyr
```

```
                 20                  25                  30
Trp Met Ser Trp Val Arg Gln Ala Pro Gly Lys Gly Leu Glu Trp Val
             35                  40                  45
Ala Asn Ile Lys Gln Asp Gly Ser Glu Lys Tyr Tyr Val Asp Ser Val
         50                  55                  60
Arg Gly Arg Phe Thr Val Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
                 85                  90                  95
Ala Arg Asp Tyr Phe Gly Ser Gly Thr Tyr Phe Phe Tyr Phe Asp Tyr
             100                 105                 110
Trp Gly Gln Gly Thr Leu Val Thr Phe Ser Ser
         115                 120

<210> SEQ ID NO 21
<211> LENGTH: 117
<212> TYPE: PRT
<213> ORGANISM: Homo sapiens

<400> SEQUENCE: 21

Gln Val Gln Leu Val Glu Ser Gly Gly Gly Val Val Gln Pro Gly Arg
 1               5                  10                  15
Ser Leu Arg Leu Ser Cys Ala Ala Ser Gly Phe Thr Phe Ser Ser Tyr
             20                  25                  30
Ala Met His Trp Val Arg Gln Ala Pro Gly Lys Gly Leu Glu Trp Val
             35                  40                  45
Ala Val Leu Trp Phe Asp Gly Ser Asn Glu Asp Tyr Ala Asp Ser Val
         50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Asp Gly Trp Gly Tyr Phe Asp Tyr Trp Gly Gln Gly Thr Leu
             100                 105                 110
Val Thr Val Ser Ser
         115

<210> SEQ ID NO 22
<211> LENGTH: 117
<212> TYPE: PRT
<213> ORGANISM: Homo sapiens

<400> SEQUENCE: 22

Gln Val Gln Leu Val Asp Ser Gly Gly Asp Val Val Gln Pro Gly Arg
 1               5                  10                  15
Ser Leu Arg Leu Ser Cys Ala Ala Ser Gly Phe Ser Phe Ser Arg Ser
             20                  25                  30
Gly Ile His Trp Val Arg Gln Ala Pro Gly Lys Gly Leu Glu Trp Val
             35                  40                  45
Ala Val Ile Trp Tyr Asp Gly Ile Tyr Lys Tyr Tyr Ala Asp Ser Val
         50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Glu Lys Asn Trp Gly Ile Asp Tyr Trp Gly Gln Gly Thr Leu
```

```
                100             105             110
Val Thr Val Ser Ser
        115

<210> SEQ ID NO 23
<211> LENGTH: 119
<212> TYPE: PRT
<213> ORGANISM: Homo sapiens

<400> SEQUENCE: 23

Glu Val Gln Leu Val Gln Ser Gly Gly Gly Leu Val His Pro Gly Gly
1               5                   10                  15

Ser Leu Arg Leu Ser Cys Ala Gly Ser Gly Phe Pro Val Ser Ser Tyr
            20                  25                  30

Gly Met His Trp Val Arg Gln Ala Pro Gly Lys Gly Leu Glu Trp Val
        35                  40                  45

Ser Ala Ile Gly Val Gly Gly Thr Tyr His Val Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Gly Asp Met Ala Val Tyr Tyr Cys Ala
                85                  90                  95

Arg Asp Pro Gly Phe Gly Glu Val Tyr Phe Asp Tyr Trp Gly Gln Gly
            100                 105                 110

Thr Leu Val Thr Val Ser Ser
        115

<210> SEQ ID NO 24
<211> LENGTH: 12
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: G or S
<220> FEATURE:
<221> NAME/KEY: MISC_FEATURE
<222> LOCATION: (6)..(6)
<223> OTHER INFORMATION: I or V
<220> FEATURE:
<221> NAME/KEY: MISC_FEATURE
<222> LOCATION: (8)..(8)
<223> OTHER INFORMATION: S or R
<220> FEATURE:
<221> NAME/KEY: MISC_FEATURE
<222> LOCATION: (9)..(9)
<223> OTHER INFORMATION: S or no amino acid
<220> FEATURE:
<221> NAME/KEY: MISC_FEATURE
<222> LOCATION: (10)..(10)
<223> OTHER INFORMATION: A, F, W or Y

<400> SEQUENCE: 24

Arg Ala Ser Gln Xaa Xaa Ser Xaa Xaa Xaa Leu Ala
1               5                   10

<210> SEQ ID NO 25
<211> LENGTH: 7
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: D or G
<220> FEATURE:
<221> NAME/KEY: MISC_FEATURE
```

```
<222> LOCATION: (4)..(4)
<223> OTHER INFORMATION: S or N
<220> FEATURE:
<221> NAME/KEY: MISC_FEATURE
<222> LOCATION: (5)..(5)
<223> OTHER INFORMATION: L or R
<220> FEATURE:
<221> NAME/KEY: MISC_FEATURE
<222> LOCATION: (6)..(6)
<223> OTHER INFORMATION: A, E or Q
<220> FEATURE:
<221> NAME/KEY: MISC_FEATURE
<222> LOCATION: (7)..(7)
<223> OTHER INFORMATION: S, T or R

<400> SEQUENCE: 25

Xaa Ala Ser Xaa Xaa Xaa Xaa
1               5

<210> SEQ ID NO 26
<211> LENGTH: 9
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: F, Y or R
<220> FEATURE:
<221> NAME/KEY: MISC_FEATURE
<222> LOCATION: (4)..(4)
<223> OTHER INFORMATION: N, G or S
<220> FEATURE:
<221> NAME/KEY: MISC_FEATURE
<222> LOCATION: (5)..(5)
<223> OTHER INFORMATION: S or N
<220> FEATURE:
<221> NAME/KEY: MISC_FEATURE
<222> LOCATION: (6)..(6)
<223> OTHER INFORMATION: Y, F, W or S
<220> FEATURE:
<221> NAME/KEY: MISC_FEATURE
<222> LOCATION: (8)..(8)
<223> OTHER INFORMATION: L or R

<400> SEQUENCE: 26

Gln Gln Xaa Xaa Xaa Xaa Pro Xaa Thr
1               5

<210> SEQ ID NO 27
<211> LENGTH: 11
<212> TYPE: PRT
<213> ORGANISM: Homo sapiens

<400> SEQUENCE: 27

Arg Ala Ser Gln Gly Ile Ser Arg Ala Leu Ala
1               5                   10

<210> SEQ ID NO 28
<211> LENGTH: 11
<212> TYPE: PRT
<213> ORGANISM: Homo sapiens

<400> SEQUENCE: 28

Arg Ala Ser Gln Ser Val Ser Ser Tyr Leu Ala
1               5                   10

<210> SEQ ID NO 29
<211> LENGTH: 11
<212> TYPE: PRT
<213> ORGANISM: Homo sapiens
```

```
<400> SEQUENCE: 29

Arg Ala Ser Gln Gly Ile Ser Arg Ala Leu Ala
1               5                   10

<210> SEQ ID NO 30
<211> LENGTH: 11
<212> TYPE: PRT
<213> ORGANISM: Homo sapiens

<400> SEQUENCE: 30

Arg Ala Ser Gln Gly Ile Ser Ser Trp Leu Ala
1               5                   10

<210> SEQ ID NO 31
<211> LENGTH: 12
<212> TYPE: PRT
<213> ORGANISM: Homo sapiens

<400> SEQUENCE: 31

Arg Ala Ser Gln Ser Val Ser Ser Ser Phe Leu Ala
1               5                   10

<210> SEQ ID NO 32
<211> LENGTH: 7
<212> TYPE: PRT
<213> ORGANISM: Homo sapiens

<400> SEQUENCE: 32

Asp Ala Ser Ser Leu Glu Ser
1               5

<210> SEQ ID NO 33
<211> LENGTH: 7
<212> TYPE: PRT
<213> ORGANISM: Homo sapiens

<400> SEQUENCE: 33

Asp Ala Ser Asn Arg Ala Thr
1               5

<210> SEQ ID NO 34
<211> LENGTH: 7
<212> TYPE: PRT
<213> ORGANISM: Homo sapiens

<400> SEQUENCE: 34

Asp Ala Ser Asn Leu Glu Arg
1               5

<210> SEQ ID NO 35
<211> LENGTH: 7
<212> TYPE: PRT
<213> ORGANISM: Homo sapiens

<400> SEQUENCE: 35

Gly Ala Ser Ser Leu Gln Ser
1               5

<210> SEQ ID NO 36
<211> LENGTH: 7
<212> TYPE: PRT
<213> ORGANISM: Homo sapiens

<400> SEQUENCE: 36
```

```
Gly Ala Ser Ser Arg Ala Thr
1               5
```

<210> SEQ ID NO 37
<211> LENGTH: 9
<212> TYPE: PRT
<213> ORGANISM: Homo sapiens

<400> SEQUENCE: 37

```
Gln Gln Phe Asn Ser Tyr Pro Leu Thr
1               5
```

<210> SEQ ID NO 38
<211> LENGTH: 9
<212> TYPE: PRT
<213> ORGANISM: Homo sapiens

<400> SEQUENCE: 38

```
Gln Gln Arg Ser Asn Trp Pro Leu Thr
1               5
```

<210> SEQ ID NO 39
<211> LENGTH: 9
<212> TYPE: PRT
<213> ORGANISM: Homo sapiens

<400> SEQUENCE: 39

```
Gln Gln Phe Asn Ser Phe Pro Leu Thr
1               5
```

<210> SEQ ID NO 40
<211> LENGTH: 9
<212> TYPE: PRT
<213> ORGANISM: Homo sapiens

<400> SEQUENCE: 40

```
Gln Gln Tyr Asn Ser Tyr Pro Arg Thr
1               5
```

<210> SEQ ID NO 41
<211> LENGTH: 9
<212> TYPE: PRT
<213> ORGANISM: Homo sapiens

<400> SEQUENCE: 41

```
Gln Gln Tyr Gly Ser Ser Pro Leu Thr
1               5
```

<210> SEQ ID NO 42
<211> LENGTH: 107
<212> TYPE: PRT
<213> ORGANISM: Homo sapiens

<400> SEQUENCE: 42

```
Val Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Arg Ala
            20                  25                  30

Leu Ala Trp Tyr Gln Gln Lys Pro Gly Lys Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
```

```
                65                  70                  75                  80
Glu Asp Phe Ala Thr Tyr Tyr Cys Gln Gln Phe Asn Ser Tyr Pro Leu
                    85                  90                  95

Thr Phe Gly Gly Gly Thr Lys Val Glu Ile Lys
                100                 105

<210> SEQ ID NO 43
<211> LENGTH: 107
<212> TYPE: PRT
<213> ORGANISM: Homo sapiens

<400> SEQUENCE: 43

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
                35                  40                  45

Tyr Asp Ala Ser Asn Arg Ala Thr Gly Ile Pro Ala Arg Phe Ser Gly
            50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                    85                  90                  95

Thr Phe Gly Gly Gly Thr Lys Val Glu Ile Lys
                100                 105

<210> SEQ ID NO 44
<211> LENGTH: 107
<212> TYPE: PRT
<213> ORGANISM: Homo sapiens

<400> SEQUENCE: 44

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Arg Ala
                20                  25                  30

Leu Ala Trp Tyr Gln Gln Lys Pro Gly Lys Ala Pro Lys Leu Leu Ile
                35                  40                  45

Tyr Asp Ala Ser Asn Leu Glu Arg Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Phe Pro Leu
                    85                  90                  95

Thr Phe Gly Gly Gly Thr Lys Val Glu Ile Lys
                100                 105

<210> SEQ ID NO 45
<211> LENGTH: 107
<212> TYPE: PRT
<213> ORGANISM: Homo sapiens

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
                20                  25                  30
```

```
Leu Ala Trp Tyr Gln Gln Lys Pro Glu Lys Ala Pro Lys Ser Leu Ile
            35                  40                  45

Tyr Gly Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Arg
                 85                  90                  95

Thr Phe Gly Gln Gly Thr Lys Val Glu Ile Lys
                100                 105
```

<210> SEQ ID NO 46
<211> LENGTH: 108
<212> TYPE: PRT
<213> ORGANISM: Homo sapiens

<400> SEQUENCE: 46

```
Glu Ile Val Leu Thr Gln Ser Pro Gly Thr Leu Ser Leu Ser Pro Gly
  1               5                  10                  15

Asp Arg Ala Thr Leu Ser Cys Arg Ala Ser Gln Ser Val Ser Ser Ser
                 20                  25                  30

Phe Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Leu Thr Phe Gly Gly Gly Thr Lys Val Glu Ile Lys
                100                 105
```

<210> SEQ ID NO 47
<211> LENGTH: 463
<212> TYPE: PRT
<213> ORGANISM: Homo sapiens

<400> SEQUENCE: 47

```
Met Glu Phe Gly Leu Asn Trp Val Phe Leu Val Ala Leu Leu Arg Asp
  1               5                  10                  15

Val Gln Cys Gln Val Gln Leu Val Glu Ser Gly Gly Gly Val Val Gln
                 20                  25                  30

Pro Gly Arg Ser Leu Arg Leu Ser Cys Ala Ala Ser Gly Phe Thr Phe
            35                  40                  45

Phe Ser Tyr Ala Met His Trp Val Arg Gln Thr Pro Gly Lys Gly Leu
         50                  55                  60

Glu Trp Val Ala Val Ile Trp Phe Asp Gly Ser Asn Glu Asn Tyr Val
 65                  70                  75                  80

Asp Ser Val Lys Gly Arg Phe Thr Ile Ser Arg Asp Asn Ser Lys Asn
                 85                  90                  95

Thr Leu Tyr Leu Gln Met Asn Thr Leu Arg Ala Glu Thr Ala Val
                100                 105                 110

Tyr Tyr Cys Ala Arg Asp Ala Trp Ser Tyr Phe Asp Tyr Trp Gly Gln
            115                 120                 125

Gly Thr Leu Val Thr Val Ser Ser Ala Ser Thr Lys Gly Pro Ser Val
        130                 135                 140
```

```
Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Lys Thr Tyr Thr Cys Asn Val Asp His Lys
210                 215                 220

Pro Ser Asn Thr Lys Val Asp Lys Arg Val Glu Ser Lys Tyr Gly Pro
225                 230                 235                 240

Pro Cys Pro Pro Cys Pro Ala Pro Glu Phe Ala Gly Gly Pro Ser Val
                245                 250                 255

Phe Leu Phe Pro Pro Lys Pro Lys Asp Thr Leu Met Ile Ser Arg Thr
                260                 265                 270

Pro Glu Val Thr Cys Val Val Val Asp Val Ser Gln Glu Asp Pro Glu
            275                 280                 285

Val Gln Phe Asn Trp Tyr Val Asp Gly Val Glu Val His Asn Ala Lys
        290                 295                 300

Thr Lys Pro Arg Glu Glu Gln Phe Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Gly Leu Pro Ser Ser Ile Glu Lys Thr Ile
                340                 345                 350

Ser Lys Ala Lys Gly Gln Pro Arg Glu Pro Gln Val Tyr Thr Leu Pro
            355                 360                 365

Pro Ser Gln Glu Glu Met Thr Lys Asn Gln Val Ser Leu Thr Cys Leu
        370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Arg Leu Thr Val Asp Lys Ser Arg
                420                 425                 430

Trp Gln Glu Gly Asn Val Phe Ser Cys Ser Val Met His Glu Ala Leu
            435                 440                 445

His Asn His Tyr Thr Gln Lys Ser Leu Ser Leu Ser Leu Gly Lys
        450                 455                 460

<210> SEQ ID NO 48
<211> LENGTH: 236
<212> TYPE: PRT
<213> ORGANISM: Homo sapiens

<400> SEQUENCE: 48

Met Asp Met Arg Val Pro Ala Gln Leu Leu Gly Leu Leu Leu Leu Trp
1               5                   10                  15

Leu Pro Gly Ala Arg Cys Val Ile Gln Leu Thr Gln Ser Pro Ser Ser
                20                  25                  30

Leu Ser Ala Ser Val Gly Asp Arg Val Thr Ile Thr Cys Arg Ala Ser
            35                  40                  45

Gln Gly Ile Ser Arg Ala Leu Ala Trp Tyr Gln Gln Lys Pro Gly Lys
```

-continued

```
                50                    55                    60
Gly Pro Lys Leu Leu Ile Tyr Asp Ala Ser Ser Leu Glu Ser Gly Val
65                      70                      75                  80

Pro Ser Arg Phe Ser Gly Ser Gly Ser Gly Thr Asp Phe Thr Leu Thr
                    85                      90                  95

Ile Ser Ser Leu Gln Pro Glu Asp Phe Ala Thr Tyr Tyr Cys Gln Gln
                100                     105                 110

Phe Asn Ser Tyr Pro Leu Thr Phe Gly Gly Gly Thr Lys Val Glu Ile
            115                     120                 125

Lys Arg Thr Val Ala Ala Pro Ser Val Phe Ile Phe Pro Pro Ser Asp
        130                     135                 140

Glu Gln Leu Lys Ser Gly Thr Ala Ser Val Val Cys Leu Leu Asn Asn
145                     150                     155                 160

Phe Tyr Pro Arg Glu Ala Lys Val Gln Trp Lys Val Asp Asn Ala Leu
                165                     170                 175

Gln Ser Gly Asn Ser Gln Glu Ser Val Thr Glu Gln Asp Ser Lys Asp
            180                     185                 190

Ser Thr Tyr Ser Leu Ser Ser Thr Leu Thr Leu Ser Lys Ala Asp Tyr
        195                     200                 205

Glu Lys His Lys Val Tyr Ala Cys Glu Val Thr His Gln Gly Leu Ser
    210                     215                 220

Ser Pro Val Thr Lys Ser Phe Asn Arg Gly Glu Cys
225                 230                 235
```

USE OF VAP-1 INHIBITORS FOR TREATING FIBROTIC CONDITIONS

CROSS REFERENCE TO RELATED APPLICATIONS

This application is a Continuation of co-pending U.S. patent application Ser. No. 13/395,029 filed on Aug. 24, 2012, which is the National Phase under 35 U.S.C. § 371 of International Application No. PCT/FI2010/050689 filed on Sep. 7, 2010, which claims the benefit under 35 U.S.C. § 119(e) to U.S. Provisional Application Nos. 61/240,402 filed Sep. 8, 2009 and 61/323,032 filed Apr. 12, 2010, all of which are hereby expressly incorporated by reference into the present application.

FIELD OF THE INVENTION

The present invention relates to inhibitors of VAP-1 and their use as anti-fibrotic agents. Furthermore, the present invention relates to a method of diagnosing a fibrotic condition and to a kit for use in said diagnostic method.

BACKGROUND OF THE INVENTION

Fibrotic conditions usually occur as a result of a disturbed woundhealing process after trauma or chronic inflammation. The fibrotic pathology is especially prevalent in organs that are on a regular basis exposed to chemical and biological insults, e.g. liver, lung, skin and kidney. Regardless if the disorder is acute or chronic they share a common characteristic of abnormal fibroblast activation and accumulation of extracellular matrix (ECM), leading to a loss of organ function as the normal tissue is replaced by scar tissue. The condition is progressive, often irreversible with a poor prognosis and survival rate.

The composition of fibrotic scarring is quite similar irrespective of the cause of injury. Diagnosis and the verification of the severity of fibrosis are of utmost importance from prognostic viewpoints. The decision-making process for treatment is highly based on the assessment of fibrosis, its progression and the onset of complications. In hepatic fibrosis, percutaneous liver biopsy is the gold standard for grading and staging of liver disease. This is, however, an invasive procedure with certain unavoidable risks and complications commonly associated with pain and discomfort. Death rates, due to complications from the procedure, range from 1:1000 to 1:10 000 (Crockett et al., 2006).

Levels of serum monoamine oxidase activity have been found to be elevated in patients with cirrhosis, chronic hepatitis and liver cancer associated with fibrosis but were found to be normal in patients with inflammatory connective tissue disorders such as rheumatoid arthritis or systemic lupus erythematosus (McEwen and Castell 1967, J Lab Clin Med. 70:36-47; Ito et al. 1971 Digestion. 4:49-58; Ma Lin et al., 1976, Proc Soc Exp Biol Med. 151:40-3). However, the elevated serum monoamine oxidase activity has been considered only as a marker or as a response to tissue injury and has not been known to have a role in the pathogenesis of fibrosis.

Conventional therapeutic approaches have largely been targeted towards the inflammatory process of fibrosis, using corticosteroids and immunosuppressive drugs. However, unfortunately these agents have little to no clinical effect and there is a clear need for new drugs to treat fibrotic conditions.

BRIEF DESCRIPTION OF THE INVENTION

Some objects of the present invention relate to VAP-1 inhibitors as anti-fibrotic agents, the uses of VAP-1 inhibitors for the manufacture of a medicament for the treatment of a fibrotic condition, and methods of preventing, treating or alleviating a fibrotic condition in a human subject in need thereof, said method comprising administering to said patient an efficient amount of a VAP-1 inhibitor.

A further object of the present invention is to provide a method of diagnosing a fibrotic condition in a subject. The method comprises a) providing a sample of a bodily fluid from said subject, b) assaying the amount of soluble VAP-1 (sVAP-1) or SSAO activity in said sample, c) diagnosing fibrosis on the basis of said amount of sVAP-1 or SSAO activity. If desired, the amount of sVAP-1 or SSAO activity may be compared to the amount of sVAP-1 or SSAO activity in a reference bodily fluid.

A still further object of the present invention is to provide a kit for use in the method of diagnosing a fibrotic condition.

In some embodiments of the above objects, the VAP-1 inhibitor is an anti-VAP-1 antibody such as a fully human anti-VAP-1 antibody comprising one to three CDR consensus sequences selected from a group consisting of SEQ ID NOs 1 to 3 and/or a light chain polypeptide comprising one to three CDR consensus sequences selected from a group consisting of SEQ ID NOs 24 to 26. In some other embodiments, said anti-VAP-1 antibody has a heavy chain polypeptide comprising a first CDR sequence selected from SEQ ID NOs 4 to 8, a second CDR sequence selected from SEQ ID NOs 9 to 13, and a third CDR sequence selected from SEQ ID NOs 14 to 18, and/or a light chain polypeptide comprising a first CDR sequence selected from SEQ ID NOs 27 to 31, a second CDR sequence selected from SEQ ID NOs 32 to 36 and a third CDR sequence selected from SEQ ID NOs 37 to 41.

In some further embodiments, said anti-VAP-1 antibody has a heavy chain variable region comprising an amino acid sequence selected from a group consisting of SEQ ID NOs 19 to 23, and a respective light chain variable region comprising an amino acid sequence selected from a group consisting of SEQ ID NOs 42 to 46. In some still further embodiments, said antibody is a recombinant fully human recombinant antibody comprising a heavy chain polypeptide depicted in SEQ ID NO 47 and a light chain polypeptide depicted in SEQ ID NO 48.

In some other embodiments of the above objects, the VAP-1 inhibitor is a SSAO inhibitor, such as a compound selected from a group consisting of hydrazine derivatives, propenyl- and propargylamines, 4-substituted-2-butynylamines, haloallylamines, pyrroline derivatives, propargyldiamines, allylamines, diamines, 4,5,6,7-tetrahydroimidazo[4,5-c]pyridine derivatives, thiocarbamoyl derivatives, carboxamides, sulfonamides, thiazole and/or guanidine derivatives, oxime derivatives, dihydrazine, arylalkylamines, oxazolidinones, haloalkylamines, benfotiamine, and imidazopyridine derivatives.

In some further embodiments of the above objects, the fibrotic condition is selected from a group consisting of liver fibrosis and the inflammatory conditions which predispose to it i.e. acute and chronic hepatitis, biliary disease and toxic liver injury, pulmonary fibrosis, renal fibrosis, including that resulting from diabetic nephropathy, myelofibrosis, pancreatic fibrosis, scleroderma, connective tissue diseases, scarring, skin fibrosis, cardiac fibrosis, organ transplant, vascular stenosis, restenosis, arterial fibrosis, arthrofibrosis, breast fibrosis, muscle fibrosis, retroperitoneal fibrosis, thyroid fibrosis, lymph node fibrosis, bladder fibrosis, pleural fibrosis and COPD, a disease in which airway walls are fibrotic with the accumulation of myofibroblasts and collagen, and like all fibrotic tissues, are contracted.

Other specific embodiments of the invention are set forth in the dependent claims.

Other objects, details and advantages of the present invention will become apparent from the following drawings, detailed description and examples.

BRIEF DESCRIPTION OF THE DRAWINGS

In the following the invention will be described in greater detail by means of preferred embodiments with reference to the attached drawings, in which FIGS. 1A and 1B demonstrate that administration of VAP-1 antibody BTT-1029 results in near full protection from CCl4 induced liver fibrosis.

FIG. 5A illustrates the effect of CCl4-induced liver fibrosis on soluble VAP-1 levels in serum analysed with a time-resolved fluorometric DELFIA assay. FIG. 5B shows that increased levels of SSAO activity were found in serum from CCl4-induced WT livers with a radiochemical assay.

FIG. 7A shows Sirius red staining of kidneys from WT and VAP-1 knockout mice injected with mineral oil (MO, control group), CCl4 or CCl4 in parallel with VAP-1 antibody are shown. In FIG. 7B, quantitative measurement of fibrotic scarring was performed using Image J threshold analysis. The mean ±SEM from three sets are shown. Magnification ×40.

DETAILED DESCRIPTION OF THE INVENTION

Figure 1A:
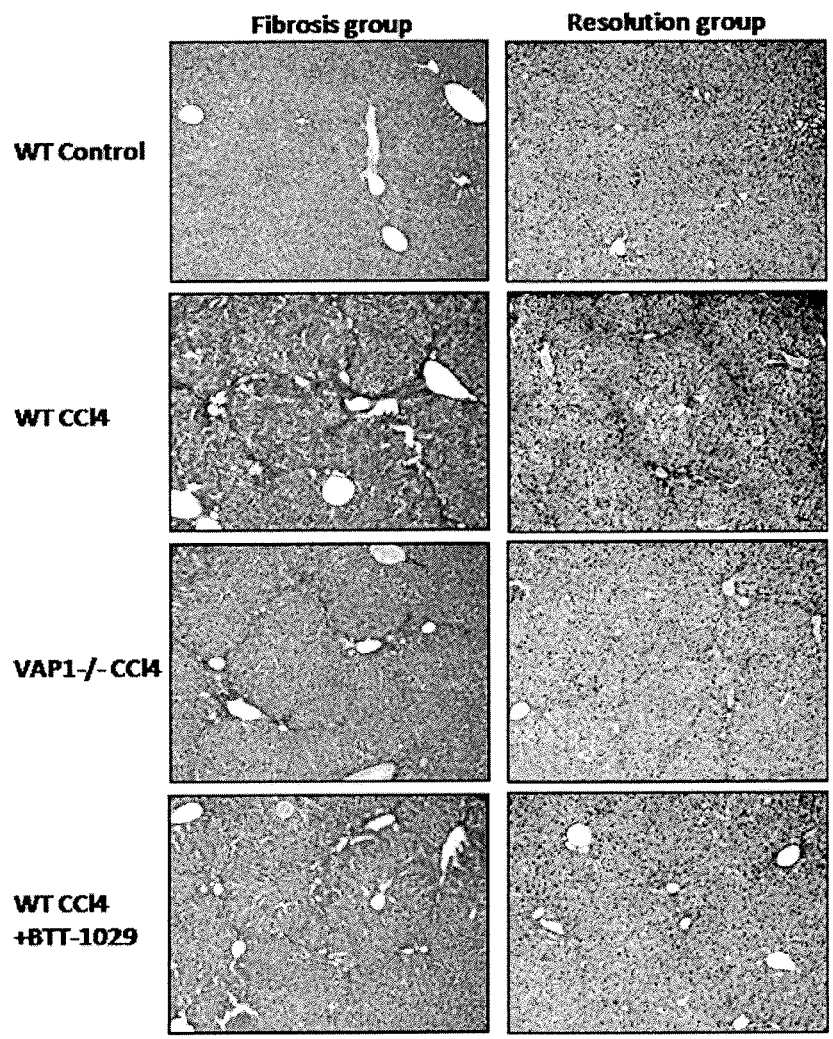
FIG. 1A shows Sirius red staining of livers from WT and VAP-1 knockout mice injected with mineral oil (MO, control group), CCl4 or CCl4 in parallel with VAP-1 antibody.

The present invention is based on a surprising finding that Vascular Adhesion Protein-1 (VAP-1), also known as semicarbazide-sensitive amine oxidase (SSAO) and defined by the human gene AOC3, plays a direct role in the formation of fibrotic tissue. To date, VAP-1 has been shown to be involved in a number of inflammatory diseases by mediating the migration of leukocytes into tissue but it has not been shown to be directly involved in the pathogenesis of fibrosis itself.

The term "fibrosis" refers to a formation or a presence of excess connective tissue in an organ or tissue. It may occur as a repair or replacement response to a stimulus such as tissue injury or inflammation.

One of the objectives underlying the present invention was to investigate the role of VAP-1 inhibitors in protecting various organs against fibrotic injury. Excellent results have been obtained e.g. in chronic fibrotic liver injury caused by carbon tetrachloride in mice, in a tobacco smoke induced mouse model of chronic obstructive pulmonary disease (COPD) and in a mouse model of vascular remodelling, vascular stenosis and neointimal thickening (fibrosis). Thus, VAP-1 inhibitors may indeed be regarded as antifibrotic agents.

In one aspect, embodiments of the present invention thus provide a method of lessening or treating fibrosis in vivo, in the human body, by administering, to a human patient in need of such treatment, an efficacious level of a VAP-1 inhibitor. The term "treatment" or "treating" is intended to include the administration of VAP-1 inhibitors to a subject for purposes which may include prophylaxis, amelioration, prevention or cure of disorders involving fibrosis, such as liver fibrosis and the inflammatory conditions which predispose to it i.e. acute and chronic hepatitis, biliary disease and toxic liver injury, pulmonary fibrosis, renal fibrosis, including that resulting from diabetic nephropathy, myelofibrosis, pancreatic fibrosis, scleroderma, connective tissue diseases, scarring, skin fibrosis, cardiac fibrosis, organ transplant, vascular stenosis, restenosis, arterial fibrosis, arthrofibrosis, breast fibrosis, muscle fibrosis, retroperitoneal fibrosis, thyroid fibrosis, lymph node fibrosis, bladder fibrosis, pleural fibrosis and COPD, a disease in which airway walls are fibrotic with the accumulation of myofibroblasts and collagen, and like all fibrotic tissues, are contracted.

By an "efficacious level" of a VAP-1 inhibitor is meant a level in which the harmful effects of fibrosis are, at a minimum, ameliorated. Amounts and regimens for the administration of VAP-1 inhibitors can be determined readily by those with ordinary skill in the clinical art of treating fibrosis-related disorders. Preferably, the VAP-1 inhibitors which are monoclonal anti-VAP-1 antibodies are provided intravascularly at intervals ranging between once weekly to once every three months at doses in the range of 0.01 to 20 mg/kg, more preferably in the range of 0.1 to 15 mg/kg, most preferably 1.0 to 10 mg/kg. Alternatively, the VAP-1 inhibitors are provided subcutaneously at intervals ranging between once weekly to once every three months at doses in the range of 0.1 to 20 mg/kg, more preferably in the range of 0.2 to 10 mg/kg, most preferably 0.5 to 5 mg/kg.

The compounds of the present invention which are inhibitors of SSAO may be administered in an effective amount within the dosage range of about 0.1 µg/kg to about 300 mg/kg, preferably between 1.0 µg/kg to 10 mg/kg. Compounds of the present invention may be administered in a single daily dose, or by kg body weight and the total daily dosage may be administered in divided doses of two, three or four times daily.

The above aspect may be formulated in an alternative way, i.e. such that some embodiments of the present invention provide VAP-1 inhibitors as antifibrotic agents for preventing, treating and/or alleviating a fibrotic condition, such as liver fibrosis and the inflammatory conditions which predispose to it ie acute and chronic hepatitis, biliary disease and toxic liver injury, pulmonary fibrosis, renal fibrosis, including that resulting from diabetic nephropathy, myelofibrosis, pancreatic fibrosis, scleroderma, connective tissue diseases, scarring, skin fibrosis, cardiac fibrosis, organ transplant, vascular stenosis, restenosis, arterial fibrosis, arthrofibrosis, breast fibrosis, muscle fibrosis, retroperitoneal fibrosis, thyroid fibrosis, lymph node fibrosis, bladder fibrosis, pleural fibrosis and COPD, a disease in which airway walls are fibrotic with the accumulation of myofibroblasts and collagen, and like all fibrotic tissues, are contracted. Accordingly, VAP-1 inhibitors may be used for the manufacture of a medicament for said fibrotic conditions.

The term "VAP-1 inhibitor" refers to any compound having the ability to block the function of VAP-1 or its SSAO activity. VAP-1 inhibitors may be divided into two main categories, blocking antibodies and SSAO inhibitors.

As used herein, the term "anti-VAP-1 antibody" (Ab) or "monoclonal anti-VAP-1 antibody" (MAb) is meant to include intact antibodies as well as antibody fragments, such as Fab and F(ab')2 fragments, which are capable of specifically binding to VAP-1 protein.

Suitable anti-VAP-1 antibodies for use in various aspects of the present invention are available in the art and further antibodies may be produced by methods known to a skilled person. For example, U.S. Pat. No. 5,580,780 describes a monoclonal antibody (mAb), 1B2, which recognizes human VAP-1 and which can block lymphocyte binding to tonsillar HEV in a frozen section assay. MAb 1B2 is a murine IgM-antibody and is specific for human VAP-1. International patent publication WO 03/093319 discloses a chimeric anti-VAP-1 monoclonal antibody BTT-1002, which has reduced immunogenicity compared to the corresponding murine antibodies. However, being a chimeric antibody its applicability to human therapy is compromised due to its immunogenicity and the resulting production of antibodies against it.

International patent publication WO 2008/129124, incorporated herein by reference, discloses fully human anti-VAP-1 antibodies with reduced immunogenicity and cytokine release. Examples of preferred fully human monoclonal anti-VAP-1 antibodies include those having a heavy chain polypeptide comprising one to three CDR consensus sequences selected from a group consisting of SEQ ID NOs 1 to 3 and/or a light chain polypeptide comprising one to three CDR consensus sequences selected from a group consisting of SEQ ID NOs 24 to 26. Other preferred anti-VAP-1 antibodies include those having a heavy chain polypeptide comprising a first CDR sequence selected from SEQ ID NOs 4 to 8, a second CDR sequence selected from SEQ ID NOs 9 to 13, and a third CDR sequence selected from SEQ ID NOs 14 to 18 and/or a light chain polypeptide comprising a first CDR sequence selected from SEQ ID NOs 27 to 31, a second CDR sequence selected from SEQ ID NOs 32 to 36 and a third CDR sequence selected from SEQ ID NOs 37 to 41.

In other embodiments of the present invention the fully human anti-VAP-1 antibody is one denoted as 8C10 and comprises a heavy chain variable region depicted in SEQ ID NO 19 and a light chain variable region depicted in SEQ ID NO 42. In still other embodiments, the anti-VAP-1 antibody is one denoted as 8A4 and it comprises a heavy chain variable region depicted in SEQ ID NO 20 and a light chain variable region depicted in SEQ ID NO 43. In further embodiments the anti-VAP-1 antibody is one denoted as 3F10 and comprising a heavy chain variable region depicted in SEQ ID NO 21 and a light chain variable region depicted in SQ ID NO 44. In still further embodiments the anti-VAP-1 antibody is one denoted as 5F12 and comprising a heavy chain variable region depicted in SEQ ID NO 22 and a light chain variable region depicted in SEQ ID NO 45. In even still further embodiments the anti-VAP-1 antibody is one denoted as 4B3 and comprising a heavy chain variable region depicted in SEQ ID NO 23 and a light chain variable region depicted in SEQ ID NO 46. These antibodies may also be provided as recombinant antibodies, such as recombinant r8C10 (BTT-1023) comprising a heavy chain polypeptide depicted in SEQ ID NO 47 and a light chain polypeptide depicted in SEQ ID NO 48.

Examples of suitable SSAO inhibitors for use in the present embodiments include, but are not limited to hydrazine derivatives such as allylhydrazines, especially phenylallylhydrazines; and hydroxylamine (i.e. aminoxy) derivatives. More specific examples of phenylallylhydrazines include but are not limited to 2-(phenyl-allyl)-hydrazine, N-[2-(4'-fluorophenyl)-allyl]-hydrazine and (E)-1-fluoro-2-phenyl-3-hydrazinopropene, whereas more specific examples of hydroxylamine derivatives include but are not limited to 2-aminooxyl-1-phenyl-ethanol, and 2-aminooxyl-1-(3',4'-dimethoxy-phenyl)-ethanol. Such SSAO inhibitors are described in WO2006/094201 and WO2005/014530 incorporated herein by reference. Other suitable hydrazine derivatives include acetohydrazides such as but not limited to 2-(4-{2-[5-(4-acetylpiperazin-1-yl)pyridine-2-yl] ethyl}phenyl)acetohydrazide described in WO 2009/145360 incorporated herein by reference; and hydrazine alcohols such as but not limited to (1R,2S)-2-(1-methylhydrazino)-1-phenyl-1-propanol, (1R, 2S)-2-(1-methylhydrazino)-1,2-diphenylethanol, 1-(1'-methylhydrazino)-3-(m-methoxyphenoxy)-2-propanol, and (1S,2R)-2-(1-methylhydrazino)-1,2-diphenylethanol (BTT-2079) described in WO 02/02090 incorporated herein by reference; and hydrazine indanes such as but not limited to (1S,2S)-2-(1-methylhydrazino)-1-indanol described in WO 03/006003 and WO2005/080319 incorporated herein by reference.

Further examples of suitable SSAO inhibitors for use in the present embodiments include, but are not limited to propenyl- and propargylamines, 4-substituted-2-butynylamines, haloallylamines (especially 2- and 3-halloallylamines), pyrroline derivatives, propargyldiamines, allylamines and diamines. More specific examples of the above SSAO inhibitors include but are not limited to 5-phenoxypenta-2,3-dienylamine, 4-(4-methoxyphenyl)but-3-ynylamine, 4-phenylbut-3-ynylamine, 2-phenyl-3-fluoroallylamine, S-(E)-4-(4-amino-2-fluorobut-2-enyloxy)-N-(1-phenylethyl)benzamide, (E)-3-fluoro-4-(4-(methylsulfonyl)phenoxy)but-2-en-1-amine, (E)-3-fluoro-4-(2-methylbenzo[d] thiazol-5-yloxy)but-2-en-1-amine, (E)-4-(4-amino-2-fluorobut-2-enyloxy)-N-(1-phenylethyl) benzenesulfonamide and (E)-2-(4-fluorophenethyl)-3-fluoroallylamine (BTT-2089, mofegeline). Such compounds are described in WO 2007/005737, WO 2005/082343, WO 2009/066152, WO 2009/055002, and Palfreyman et al., J Neural Transm. (1994), 41, 407-414), which are all incorporated herein by reference.

Still further examples of suitable SSAO inhibitors for use in the present embodiments include, but are not limited to 4,5,6,7-tetrahydroimidazo[4,5-c]pyridine derivatives (described in WO 02/38153 incorporated herein by reference), carboxamides such as N-hydroxy-2-(2-(2-methyl-1H-indol-3-yl)acetamido)acetamide and 5-amino-2-hydroxy-N-(2-hydroxybenzyl)benzamide and sulfonamides such as N2-{[4-(1,1-dimethylpropyl)phenyl]sulfonyl}-N1-hydroxyserinamide, described in WO2006/013209 and US2007/066646 incorporated herein by reference.

Furthermore, thiazole and/or guanidine derivatives, especially 2-acylaminotriazole derivatives are suitable for use in various embodiments of the present invention. More specific examples of such SSAO inhibitors include but are not limited to N-{4-[2-(4-{[amino(imino)methyl] amino}phenyl)ethyl]-1,3-thiazol-2-yl}acetamide, N-{4-[2-(4-{[amino(imino)methyl]amino}phenyl)ethyl]-5-[4-(methylsulfonyl)benzyl]-1,3-thiazol-2-yl}acetamide, N-{4-[2-(4-{[2-amino-1H-imidazol-4-yl)methyl]phenyl}ethyl)thiazol-2-yl]-acetamide, 2-(4-{2-[2-(acetylamino)-1,3-thiazol-4-yl] ethyl}phenyl)-N-[amino(imino)methyl]acetamide. Such compounds are described in WO2004/087138, WO2004/067521, WO2006/028269, WO2006/011631, and WO2005/089755, all incorporated herein by reference.

In addition, various oxime derivatives are SSAO inhibitors and may thus be used in various embodiments of the present invention. Such oxime derivatives include but are not limited to 5-bromo-1,3-benzodioxole-4-carbaldehyde oxime, 6-ethoxy-1,3-dimethyl-2,4-dioxo-1,2,3,4-tetrahydropyrimidine-5-carbaldehyde oxime, 1,3-dimethyl-6-(methylthio)-2,4-dioxo-1,2,3,4-tetra-hydropyrimidine-5-carbaldehyde oxime described in WO 2010/029379 incorporated herein by reference.

Also dihydrazine, arylalkylamines, oxazolidinones, haloalkylamines, and benfotiamine (vitamin B1) disclosed in WO 2010/015870, WO 2005/072738, Lyles G. A., Int. J. Biochem. Cell Biol. Vol. 28 pp259-276 (1996), and McDonald et al., Annual reports in Med. Chem. Vol. 42 pp. 229-243 (2007)), all incorporated herein by reference, may be used as SSAO inhibitors in various embodiments of the present invention.

Further SSAO inhibitors suitable for use in various aspects and embodiments of the present invention include imidazopyridine derivatives described in WO 2010/064020 incorporated herein by reference.

Furthermore, suitable SSAO inhibitors for use in various embodiments of the present invention include any stereoisomer, mixture of stereoisomers, E or Z forms, mixture of E and Z forms, prodrug, metabolite, crystalline form, non-crystalline form, hydrate, solvate or salt thereof having an ability to inhibit or block the SSAO activity of VAP-1.

Other suitable SSAO inhibitors may be screened and identified with SSAO assays known in the art. Such an assay may include the VAP-1 SSAO activity assay using a coupled colorimetric method essentially as described for monoamine oxidase and related enzymes (Holt, A., et al., Anal. Biochem. 244:384-392 (1997)). The SSAO activity of endothelial cells can also independently be measured using Amplex Red reagent (10-acetyl-3,7-dihydroxyphenoxazine), a highly sensitive and stable probe for $H_2O_2$ (Zhou M, Panchuk-Voloshina N. Anal Biochem. 253(2):169-74 (1997)). In addition, the amine oxidase activity can be assayed radiochemically using [7-14C]-benzylamine hydrochloride as a substrate (Jaakkola et al., Am J Pathol:155(6):1953-65 (1999)). As a source of VAP-1 SSAO enzyme, recombinant human VAP-1 SSAO expressed in cell lines such as Chinese Hamster Ovary (CHO) cells can be used (Smith, D. J., et al., J. Exp. Med. 188:17-27 (1998)). Other suitable SSAO VAP-1 enzyme sources may be serum and tissue samples from different species such as primates and rodents.

For use in accordance with the present embodiments, VAP-1 inhibitors may be provided as a pharmaceutical composition comprising a pharmaceutically acceptable carrier or diluent and, as active ingredient, a VAP-1 inhibitor. The composition contains the VAP-1 inhibitor in an amount sufficient to antagonize (fully or partially) the patient's SSAO activity or native VAP-1 binding to the biological ligands of VAP-1 in patients in need of such antagonizing.

Amounts and regimens for the administration of VAP-1 inhibitors may be determined readily by those with ordinary skill in the clinical art of treating fibrosis-related disorders. Generally, the dosage of the VAP-1 inhibitor treatment will vary depending on considerations such as: age, gender and general health of the patient to be treated; kind of concurrent treatment, if any; frequency of treatment and nature of the effect desired; extent of tissue damage; duration of the symptoms; and other variables to be adjusted by the individual physician. A desired dose can be administered in one or more applications to obtain the desired results. Pharmaceutical compositions according to the present embodiments may be provided in unit dosage forms.

The pharmaceutical compositions may be administered in any appropriate pharmacological carrier for administration. They can be administered in any form that effect prophylactic, palliative, preventive or curing conditions of fibrotic conditions in human or animal patients.

Pharmaceutical compositions for parenteral and topical administration include sterile aqueous or non-aqueous solvents, suspensions and emulsions. Examples of non-aqueous solvents are propylene glycol, polyethylene glycol, vegetable oil, fish oil, and injectable organic esters. Aqueous carriers include water, water-alcohol solutions, including saline and buffered medial parenteral vehicles including sodium chloride solution, Ringer's dextrose solution, dextrose plus sodium chloride solution, Ringer's solution containing lactose, or fixed oils. Intravenous vehicles include fluid and nutrient replenishers, electrolyte replenishers, such as those based on Ringer's dextrose and the like. Aqueous compositions according to the embodiments may comprise suitable buffer agents, such as sodium and potassium phosphates, citrate, acetate, carbonate or glycine buffers depending on the targeted pH-range. The use of sodium chloride as a tonicity adjuster is also useful. Compositions may include other excipients, such as stabilizing agents or preservatives. Useful stabilizing excipients include surfactants (polysorbate 20 & 80, poloxamer 407), polymers (polyethylene glycols, povidones), carbohydrates (sucrose, mannitol, glucose, lactose), alcohols (sorbitol, glycerol propylene glycol, ethylene glycol), suitable proteins (albumin), suitable amino acids (glycine, glutamic acid), fatty acids (ethanolamine), antioxidants (ascorbic acid, cysteine etc.), chelating agents (EDTA salts, histidine, aspartic acid) or metal ions (Ca, Ni, Mg, Mn). Among useful preservative agents are benzyl alcohol, chlorbutanol, benzalkonium chloride and possibly parabens.

The pharmaceutical composition may be provided in concentrated form or in form of a powder to be reconstituted on demand. In such cases formulations of powder for solution for injection/infusion excipients mentioned above may be used. In case of lyophilizing, certain cryoprotectants are preferred, including polymers (povidones, polyethylene glycol, dextran), sugars (sucrose, glucose, lactose), amino acids (glycine, arginine, glutamic acid) and albumin. If solution for reconstitution is added to the packaging, it may consist e.g., of pure water for injection or sodium chloride solution or dextrose or glucose solutions.

The therapeutically useful anti-VAP-1 antibodies may be conjugated, either chemically or by genetic engineering, to other agents, which provide targeting of the antibodies to a desired site of action. Alternatively, other compounds may be conjugated, either chemically or by genetic engineering, to the antibodies, so as to enhance or provide additional properties to the antibodies, especially properties, which enhance the antibodies' ability to promote alleviation of harmful effects mediated by VAP-1 binding.

The anti-VAP-1 antibodies may be labelled, either chemically or by genetic engineering, to provide detectable antibodies. Such labelled antibodies will be useful tools for imaging fibrotic sites in humans, especially for in vivo immunoscintigraphic imaging of fibrotic sites. For imaging purposes, the use of antibody fragments may be preferable to the whole antibody approach to anti-fibrotic therapy and fragments derived from fully human antibodies should still be safer than their chimeric or mouse equivalents.

Some aspects of the present invention relate to the diagnosis of fibrotic conditions. In connection with the present invention it has been found that elevated levels of soluble VAP-1 (sVAP-1) in bodily fluids (such as serum or plasma) and, consequently, elevated SSAO activity correlate with the degree of fibrosis. Some embodiments of the present invention thus provide means and methods for diagnosing fibrotic conditions such as liver fibrosis and the inflammatory conditions which predispose to it i.e. acute and chronic hepatitis, biliary disease and toxic liver injury, pulmonary fibrosis, renal fibrosis, including that resulting from diabetic nephropathy, myelofibrosis, pancreatic fibrosis, scleroderma, connective tissue diseases, scarring, skin fibrosis, cardiac fibrosis, organ transplant, vascular stenosis, restenosis, arterial fibrosis, arthrofibrosis, breast fibrosis, muscle fibrosis, retroperitoneal fibrosis, thyroid fibrosis, lymph node fibrosis, bladder fibrosis, pleural fibrosis and COPD, a disease in which where airway walls are fibrotic with the accumulation of myofibroblasts and collagen, and like all fibrotic tissues, are contracted.

In some embodiments, diagnosis of fibrotic conditions on the basis of elevated sVAP-1 levels and/or SSAO activity in bodily fluids may be combined with analysis of existing panels of predictive biomarkers for fibrotic conditions. This may improve the diagnostic capacity of the existing biomarkers. In other words, sVAP-1 levels/SSAO activity may be used either alone or in combination with other clinical and biochemical markers as a novel non-invasive test to predict the presence of fibrosis.

Level of sVAP-1 in a body fluid sample such as serum may be determined by the following method: The time-resolved one-step immunofluorometric assay (TR-IFMA) (DELFIA) for quantification of soluble VAP-1 utilizes biotin-conjugated mouse anti-human VAP-1 antibody TK8-14 (Biotie Therapies Corp.) as a capturer on a streptavidin coated microtiter plate. Detection of bound soluble VAP-1 is done using europium-conjugated mouse anti-human VAP-1 antibody TK8-18 (Biotie Therapies Corp.) as a tracer. The label is detected by measuring the time-resolved fluorescence (Victor3 multilabel counter) at 615 nm. The fluorescence counts directly correlate with how much soluble VAP-1 is present in the sample. The sample data are then analyzed in comparison to the standard curve of a reference.

In some embodiments of the present invention, fibrosis is diagnosed on the basis of SSAO activity in a bodily fluid obtained from a subject in need of such diagnosing and/or suspected to suffer from fibrosis. One suitable method for this purpose has been disclosed by Li et al. in J. Chromatogr. B, 810 (2004) 277-282. Other means and methods of determining the SSAO activity are known in the art.

Furthermore, some aspects of the present invention provide a kit for use in diagnosis of fibrosis. In some embodiments, the kit comprises one or more reagents for assessing the amount sVAP-1, such as a specific anti-VAP-1 antibody, e.g. one of the anti-VAP-1 antibodies mentioned above. In other embodiments, the kit comprises one or more reagents for assessing the SSAO activity in a bodily fluid such as serum or plasma. For instance, the kit may comprise a substrate for VAP-1 SSAO, such as benzylamine, methylamine, aminocetone or other aliphatic or aromatic monoamines, together with a suitable SSAO enzyme activity assay buffer, and a set of reagents and method for detecting SSAO activity. SSAO activity may be detected using a coupled assay in which the generation of hydrogen peroxide from the action of SSAO activity on monoamine substrates is measured, or it may be measured directly by the monitoring the conversion of a water soluble amine to an organic solvent soluble aldehyde using a $^{14}C$ labelled amine substrate, such as benzylamine.

It will be obvious to a person skilled in the art that, as technology advances, the inventive concept can be implemented in various ways. The invention and its embodiments are not limited to the examples described below but may vary within the scope of the claims.

EXAMPLE 1

Effects of VAP-1 Inhibitors in Mouse Model of Liver Fibrosis

The aim of the study was to assess the effect of VAP-1 inhibitors on fibrotic liver injury in mouse.

All mice were maintained and housed under conventional conditions at the Biomedical services unit at the University of Birmingham, according to Home Office regulations. Four mice were housed per cage and acclimated to the housing situation for one week before the experiments. Female C57BL/6 and VAP-1−/− mice (AOC3 gene knockout mice lacking VAP-1) of the age of 8-10 weeks were used in the study. C57BL/6 mice were obtained from a stock colony from the Biomedical services unit at the University of Birmingham, whereas VAP-1−/− (AOC3 gene knockout) mice were obtained from the contract breeder Taconic, Denmark.

A mouse model of chronic hepatic fibrosis was established by i.p. administration of carbon tetrachloride (CCl4; Aldrich Chemical) at a dose of 1 ml/kg dissolved in mineral oil bi-weekly for 8 weeks, whereas the control group only received mineral oil. Mice treated with a mouse anti-mouse VAP-1 antibody BTT-1029 received weekly i.v. injections two weeks prior to and during the CCl4 administration. Animals were terminated 96 h after the ultimate dose of CCl4. Blood samples were withdrawn by cardiac puncture during isoflurane anaesthesia, after which mice were culled by cervical dislocation. Livers were dissected and cut into 4 pieces for different processing.

Statistical ANOVA was done using SPSS for Windows version 11.0. One-way ANOVA followed by Fisher's least significant difference post hoc test was used for analysis of significance in samples with more than two variable groups.

Liver specimens were fixed in 4% paraformaldehyde, embedded in paraffin and cut into 4 µm sections. Sections for histopathological analysis were either Sirius red- or H&E stained according to standard procedures. For immunofluorescence staining, the fixed mouse livers were cryo-protected by immersion in 30% sucrose, quickly frozen down and cut in a cryostat at 7 µm. Briefly, sections were washed with phosphate buffered saline containing 0.1% Triton X-100 (PBST) for 10 minutes and incubated 1 hour at room temperature with 10% goat serum in 0.1% PBST. Following incubation with primary antibodies for elastin, collagen IV and laminin (Abcam) diluted in serum-PBST, slides were washed three times in PBST and incubated with secondary antibody (Invitrogen) for 1 hour at room temperature.

Figure 1B:
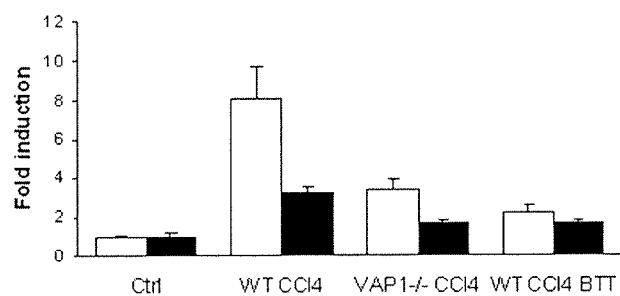
In FIG. 1B, quantitative measurement of fibrotic scarring was performed using Image J threshold analysis. The mean ±SEM from three sets are shown. Magnification ×10.
Figure 2:
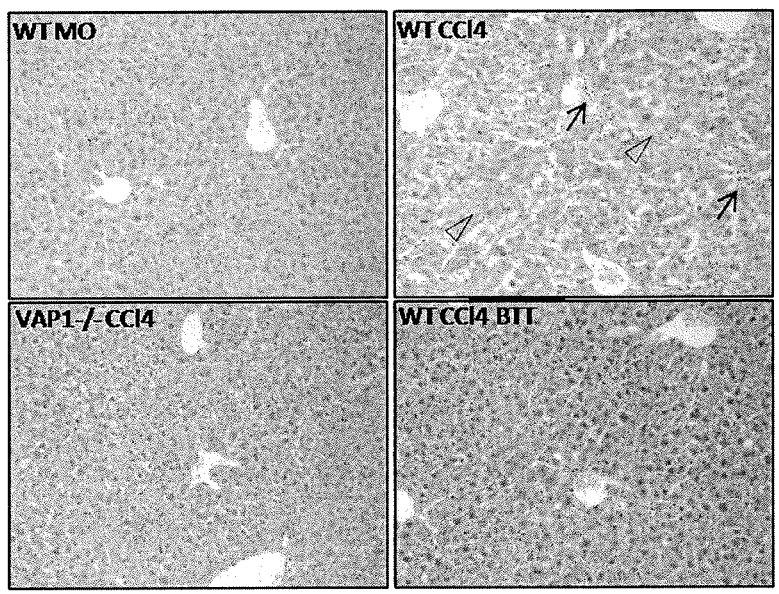
FIG. 2 demonstrates that VAP-1 antibody treated livers and VAP-1 knockout livers show a prominent lack of hepatitis and necrotic areas despite CCl4-fibrosis induction. Hematoxylin and eosin staining at ×20 magnification highlighting necrotic hepatocytes (arrowheads) and ongoing hepatitis (arrows) is shown.

As expected, CCl4 induced severe fibrotic injury in C57BL/6 mice. By 8 weeks wild type mice showed an eightfold increase in the hepatic content of Sirius red fibrils with necrosis of the hepatocytes and ongoing hepatitis. Interestingly, there was a significant decrease in fibrotic injury in both VAP-1 deficient mice and BTT-1029 treated wild type mice. These mice displayed only low amounts of Sirius red fibrils and the liver histology appeared near normal with the total absence of necrotic areas and only minor hepatitis (FIGS. 1 and 2). Furthermore, there were significantly lower numbers of mature macrophages present, once again indicating a much less severe injury compared to the wild type (data not shown).

The mRNA levels of genes related to hepatic stellate cell activation in the liver were assessed by qRT-PCR. To this end, total RNA was extracted from mouse livers using Qiagen RNAEASY® Mini Kit (#74104). RNA was reverse transcribed to cDNA templates using random primers (Promega) and SUPERSCRIPT® III from Invitrogen. Parameters for the qRT-PCR were as follows: denaturation 95° C. for 10 min, amplification 95° C. for 10 s, 55° C. for 30 s, 72° C. for 1s, 55 cycles. Quantitative Real-time PCR was measured with a Roche LIGHTCYCLER® 480 system using the reference gene GAPDH and probes from Roche. Expression levels were quantified using the 'E-method' (Roche).

Figure 3A:
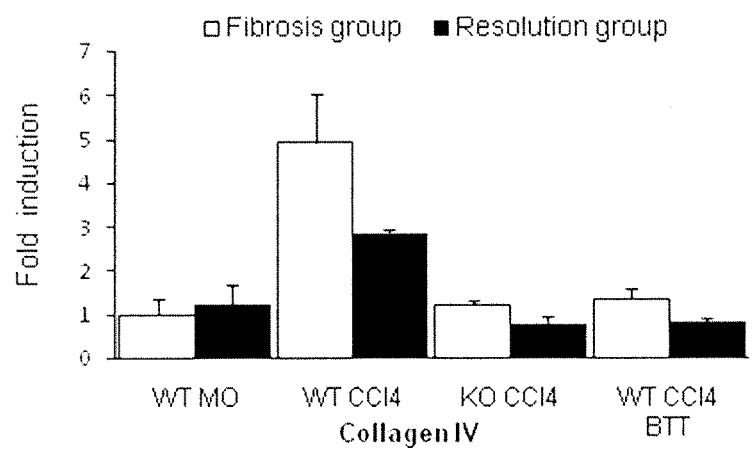
FIGS. 3A and 3C demonstrate that increase of collagen IV and elastin expression in fibrotic tissues is prevented by VAP-1 antibody. Quantitative measurements of collagen IV (FIG. 3A), elastin (FIG. 3C) and laminin (FIG. 3B) staining were performed using Image J threshold analysis. The mean ±SEM from three sets are shown.
Figure 3B:
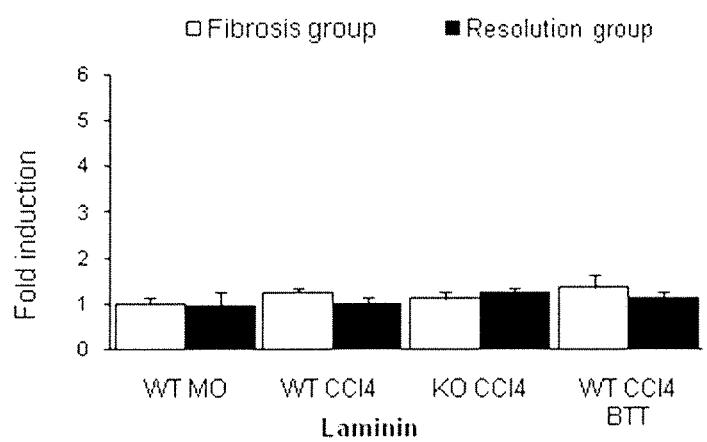
Figure 3C:
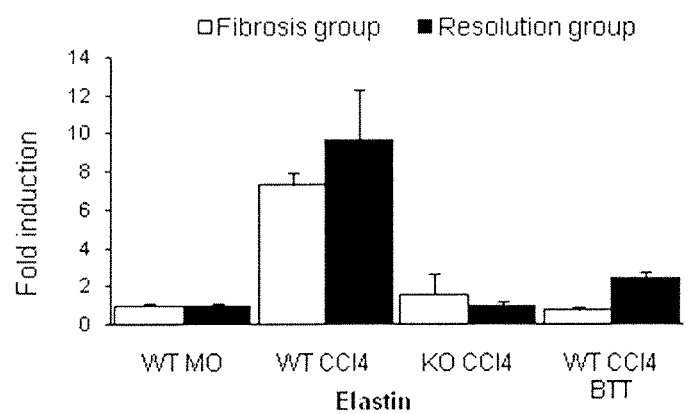
Figure 4A:
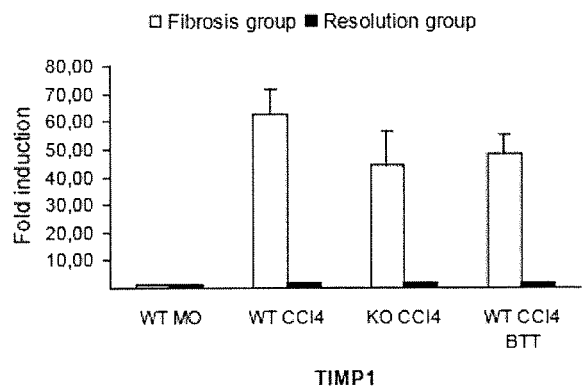
FIGS. 4A, 4B, 4C and 4D demonstrate that mRNA levels indicate a regulatory effect of VAP-1 on hepatic stellate cells and fibroblasts. Quantitative RT-PCR analysis of elastin (FIG. 4C), aSMA (FIG. 4B), VAP-1 (FIG. 4D) and TIMP1 (FIG. 4A) is shown. The data is displayed as mean ±SEM from three mice measured three times. $*p<0.05$, $<0.01$, $*<0.001$ (ANOVA).
Figure 4B:
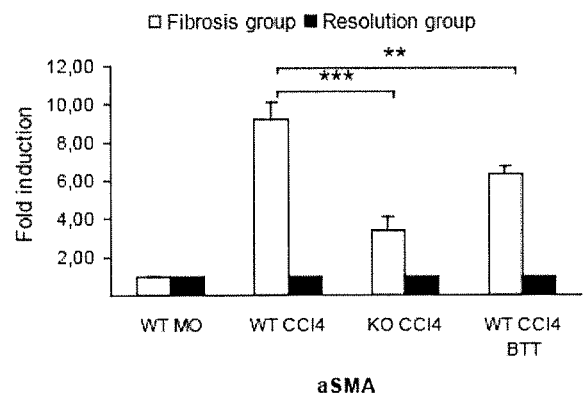
Figure 4C:
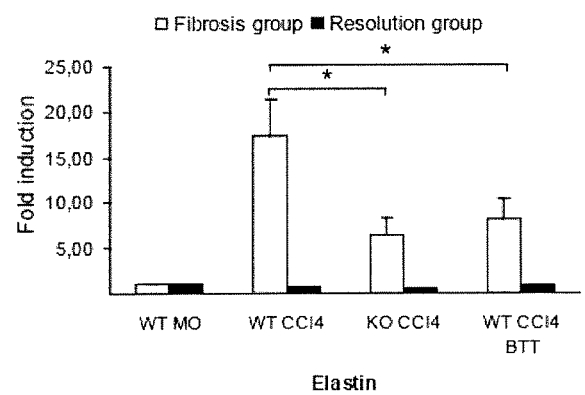
Figure 4D:
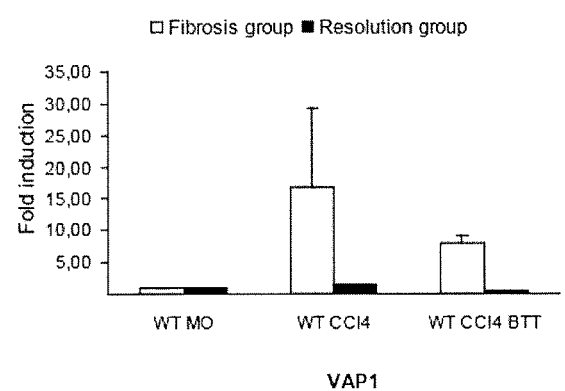

The data indicate a role for VAP-1 in the development of liver fibrosis by regulation of the hepatic stellate cells (HSC). Activated HSC are regarded as the principal source for synthesising ECM components in fibrotic liver, including elastin. CCl4 administered wild type livers showed a profound increase in aSMA and elastin mRNA levels, indicating an accumulation of aSMA expressing HSCs and deposition of elastin (FIG. 4). The mRNA levels of both αSMA and elastin in BTT-1029 treated wild type and VAP-1−/− livers were significantly lower compared to the wild type liver. The differences in elastin and collagen IV expression were also confirmed by confocal microscopy, whereas laminin levels remained unchanged (FIG. 3).

In conclusion, the BTT-1029 treatment induced an almost complete protection of established liver fibrosis by decreasing the activation of hepatic stellate cells, hence restricting the development of fibroblasts in fibrotic lesions. The same effect was also demonstrated in VAP-1−/− mice, showing a near full protection against CCl4 induced injury. The results indicate VAP-1 as a key player in the development of liver fibrosis through regulatory effects on the hepatic stellate cells. VAP-1 SSAO is a copper amine oxidase and thus analogous to lysyl oxidase, another copper amine oxidase enzyme responsible for crosslinking ECM protein such as elastin and collagen. It remains possible that the SSAO activity of VAP-1 also has a direct effect on the formation of cross links in ECM proteins.

Figure 5A:
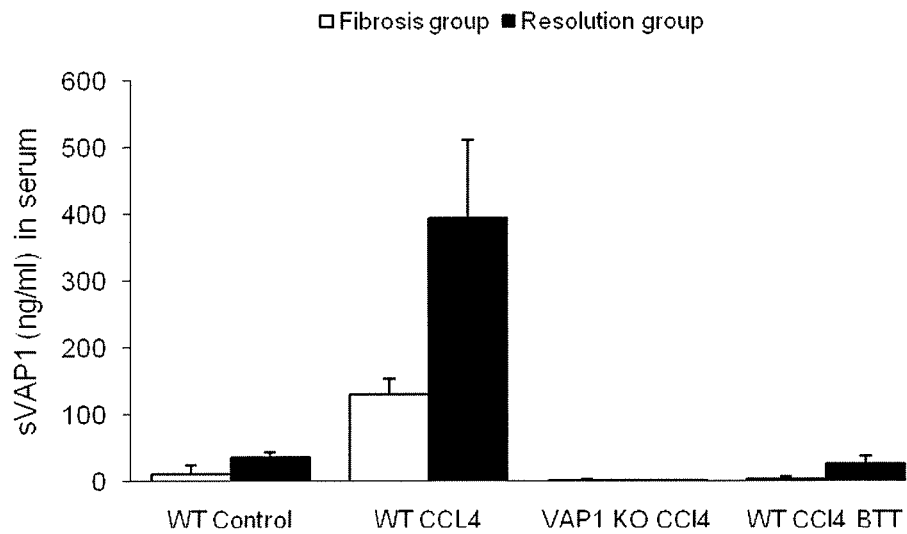
FIGS. 5A and 5B demonstrate that soluble VAP-1 and SSAO activity in serum increase in response to CCl4 induced liver fibrosis.
Figure 5B:
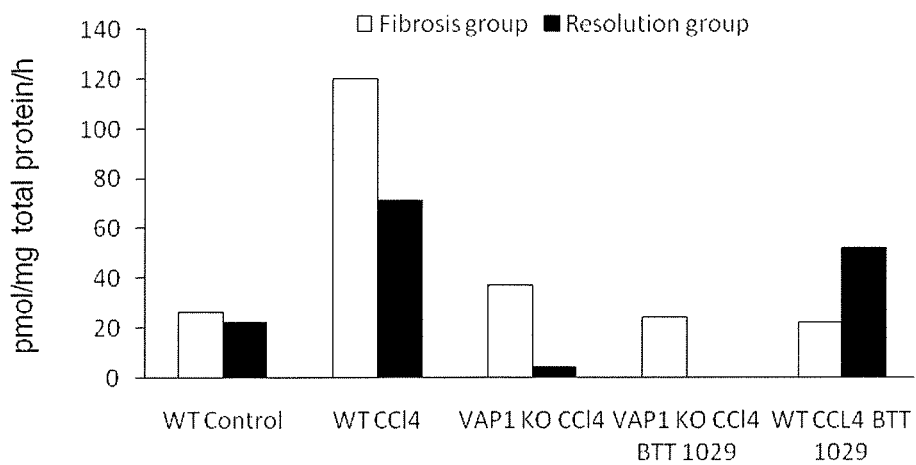

Furthermore, SSAO activities of the serum and liver tissue samples were assayed radiochemically using [7-$^{14}$C]-benzylamine hydrochloride (spec. act. 57 mCi/mmol) as a substrate (FIG. 5). Serum (40 mg/ml protein) or tissue preparations (2 mg/ml protein) were preincubated with 5 µM clorgyline and pargyline, and with non-specific binding tubes also with 1 mM semicarbazide at 37° C. for 30 min. The assay was performed at 37° C. for one hour in the final volume of 200 µl of 0.2 mM Na-phosphate buffer (pH 7.4) containing [7-$^{14}$C]-benzylamine as a substrate. The catalytic enzyme activity reaction assays were stopped and treated as have been described before in Jaakkola et al., 1999 (American Journal of Pathology, 155, 6). Protein concentrations were assayed according to Bradford et al. (Bradford, M. M., 1976, Anal. Biochem. 72, 248) using bovine serum albumin as a standard.

The results demonstrated that in addition to preventing CCl4-induced liver fibrosis, the BTT-1029 treatment markedly decreases the SSAO activity in said liver samples.

EXAMPLE 2

Renoprotective Effects of VAP-1 Inhibitors in Mouse Model of Renal Damage

High exposure to carbon tetrachloride causes damage to both liver and kidneys. Therefore, kidneys from CCl4 treated animals described in Example 1 were collected and analysed for the effect of VAP-1 inhibitors on nephropathy.

Kidneys were fixed in 4% paraformaldehyde, embedded in paraffin and cut into 4 μm sections. Histopathological analysis was done on Sirius red and H&E stained sections. Staining was performed according to standard procedures. The amount of Sirius red fibrils were quantified by threshold analysis using Image J software.

Statistical ANOVA was performed using SPSS Windows, version 11.0. One-way ANOVA followed by Tukey HSD's least significant difference post hoc test was used for analysis of significance in samples with more than two variable groups.

Figure 6:
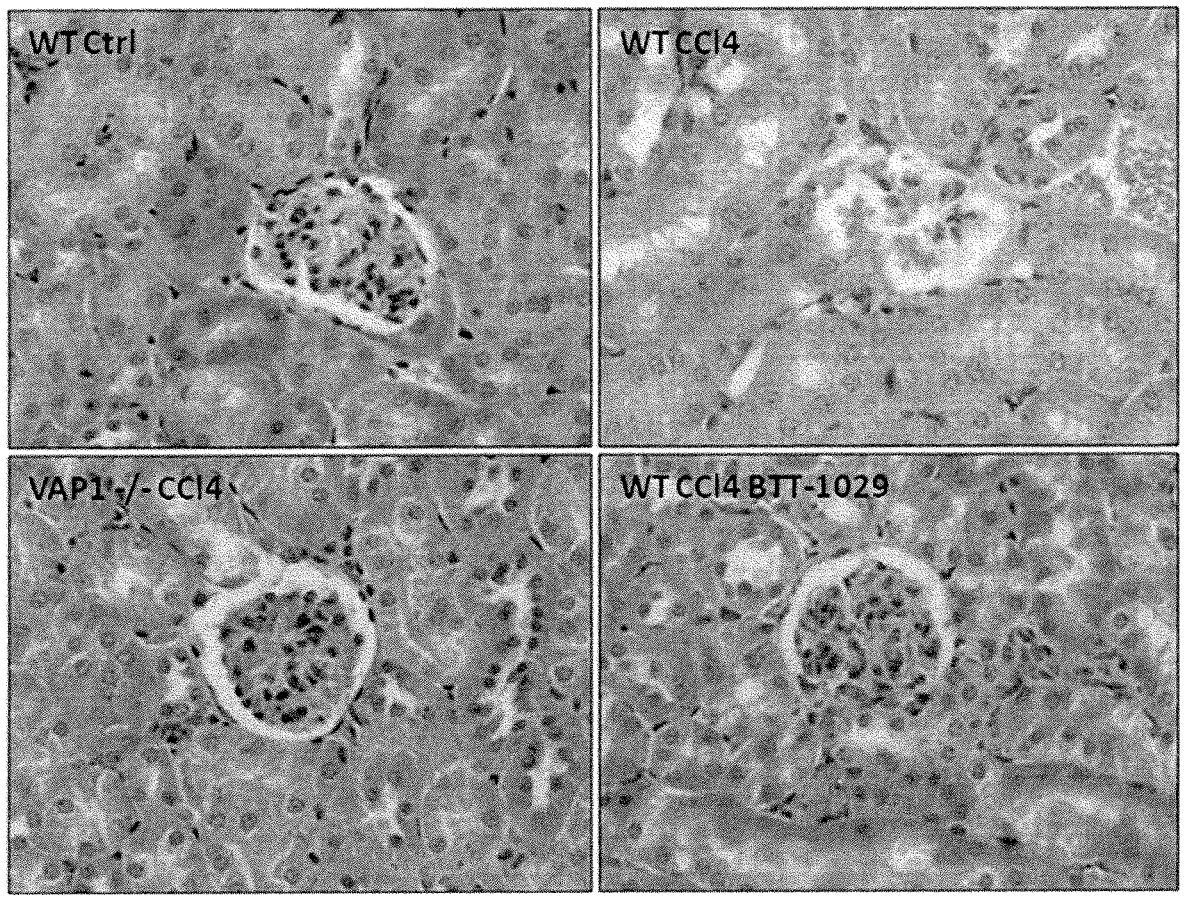
FIG. 6 demonstrates that glomerular lesions induced by CCl4 are rescued in VAP-1 knockout mice and VAP-1 antibody treated C57BL/6 mice. Hematoxylin and eosin staining at ×40 magnification highlighting the glomerulus are shown.

Mice administered CCl4 displayed focal glomerular changes with both segmental and global alterations. H&E staining demonstrated various lesions e.g. mesangial hypercellularity, adhesion and sclerosis of the tip domain. However, global collapse of the glomerular tuft with only remaining fragments of the glomerulus was mostly seen (data not shown). Interestingly, VAP-1 knockout mice and BTT-1029 treated mice were totally protected from the glomerular lesions (FIG. 6).

Figure 7A:
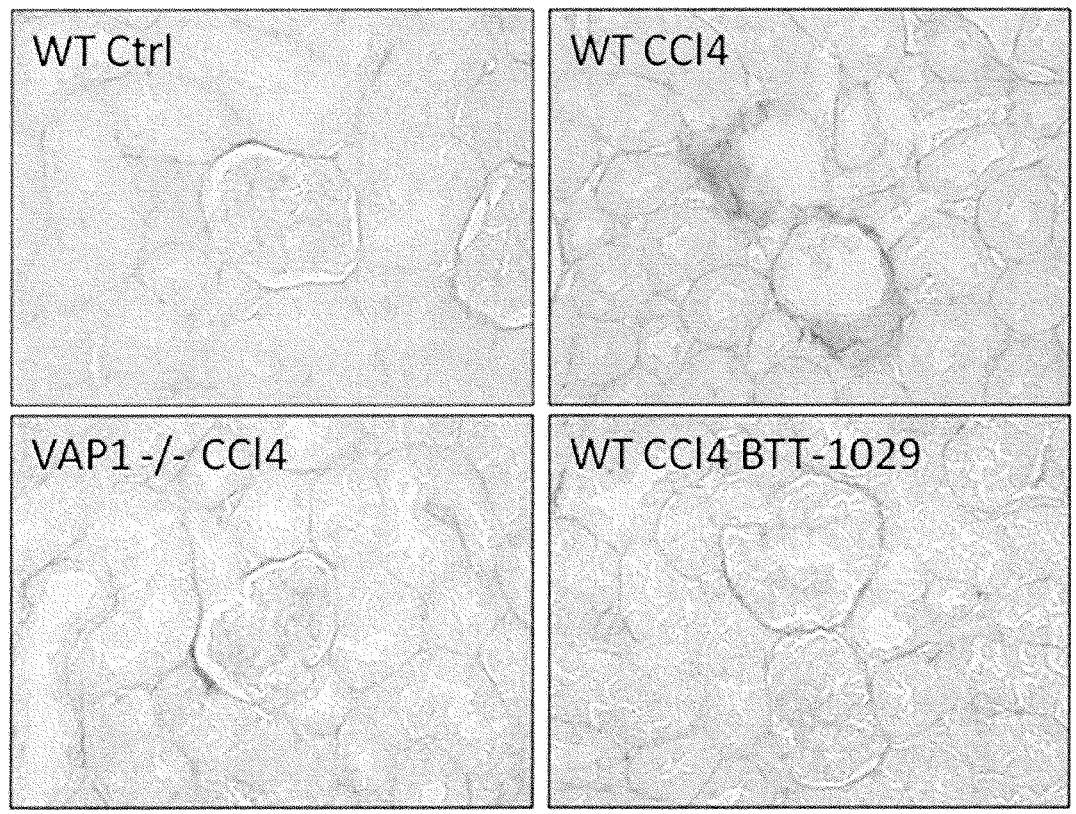
FIGS. 7A and 7B demonstrate that collagen accumulation, as a result of CCl4 induced glomerular fibrosis, is significantly reduced in VAP-1 knockout mice and VAP-1 antibody treated mice.
Figure 7B:
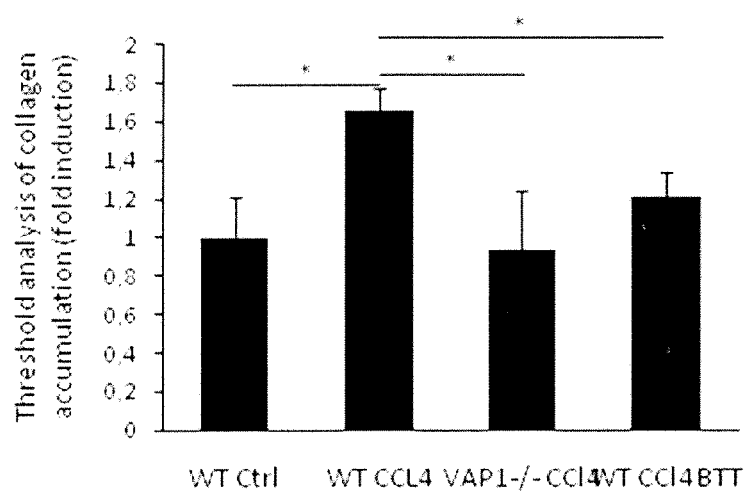

Accumulation of collagen around the glomeruli, as an indication of fibrosis, was assessed by Sirius red staining. Administration of CCl4 in C57BL/6 mice induced an almost two fold increase in collagen accumulation around the glomerular tuft. Interestingly, mice lacking VAP-1 or administered with VAP-1 inhibitor demonstrated a significant decrease in collagen deposits similar to the control (FIG. 7). The results clearly demonstrate the protective role of VAP-1 in CCl4 induced nephropathy.

EXAMPLE 3

Effects of VAP-1 Inhibitors in Mouse Model of COPD

The tobacco smoke induced mouse model of COPD was employed to assess the effect of VAP-1 inhibitors on the treatment of COPD.

C57BL/6J mice were exposed once daily to tobacco smoke (TS) for 11 consecutive days resulting in pulmonary inflammation 24 hours following the final TS exposure. After 11 days the response comprised of significant increases in macrophages, epithelial cells, eosinophils, neutrophils and lymphocytes.

Mice were randomly divided into study groups (n=10) and treated with a vehicle (5 ml/kg PBS pH 7.4+0.1% Polysorbate 80) or mouse monoclonal anti-VAP-1 antibody (3 mg/kg or 9 mg/kg BTT-1029 in the vehicle) intravenously on Days −1, 3, 6, and 9 at 4 h post TS exposure. Another group (n=10) received the vehicle intravenously and was exposed to air for an equivalent length of time. Two further groups of mice (n=10) received another vehicle (0.5% carboxymethylcellulose, sodium salt (CMC) in sterile water) or a reference compound (5 mg/kg Roflumilast in 0.5% CMC) orally once a day for 11 consecutive days at 1 h prior to each TS exposure. A final group (n=10) received the oral vehicle (0.5% CMC) and was exposed to air for an equivalent length of time.

All results were presented as individual data points for each animal and the mean value calculated for each group. Where tests for normality were positive the data initially was subjected to a one way analysis of variance test (ANOVA), followed by a Bonferroni correction for multiple comparisons in order to test for significance between treatment groups. A "p" value of ≤0.05 was considered to be statistically significant.

All data was also subjected to the Bartlets test for equal variances and for the majority of studies variances were generally equal, however as occurred in this study, occasionally some treatment groups would give a positive result. Non parametric analyses were therefore also used. As the data was normally distributed, parametric analyses (ANOVA) were quoted.

Percentage inhibitions were automatically calculated within the Excel spreadsheets for the cell data using the formula below:

$$\% \text{ Inhibition} = 1 - \left(\frac{\text{Treatment group result} - \text{sham group result}}{\text{TS vehicle group result} - \text{sham group result}}\right) \times 100$$

Figure 8:
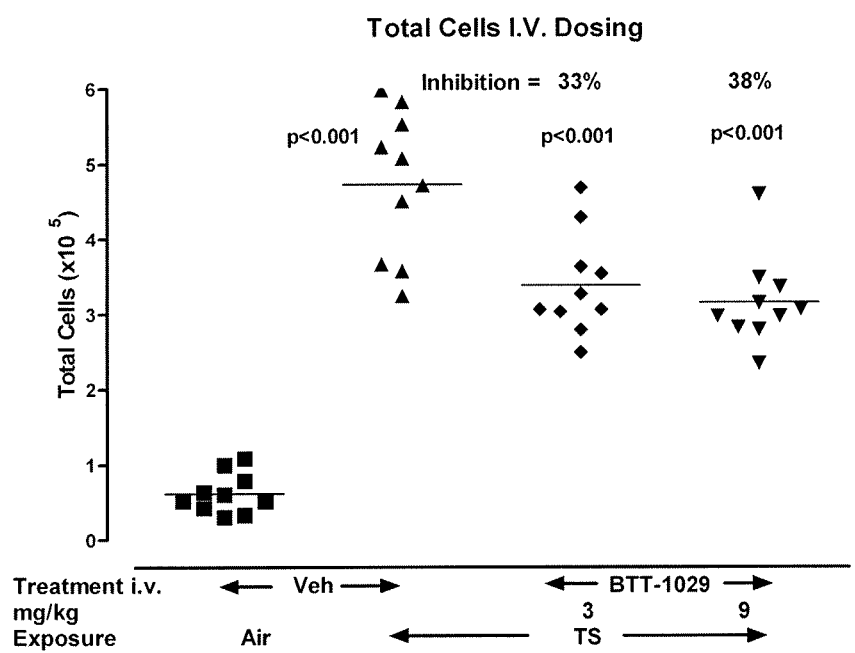
FIG. 8 illustrates reduction in total cell counts in bronchoalveolar lavage fluid from VAP-1 antibody (BTT-1029) treated tobacco smoke exposed mice compared to vehicle treated mice.

BTT-1029, when given intravenously at 9 and 3 mg/kg 4 hours post TS exposure on days −1, 3, 6 & 9 of the study, significantly reduced the TS induced cell increases in BAL (38% and 33% inhibition respectively, p<0.001 for both) (FIG. 8). This consisted of marked reductions in macrophages, (29% and 22% inhibition, p<0.01 & p<0.05 respectively), neutrophils (66 and 59% inhibition, p<0.001 for both), lymphocytes (69% and 54% inhibition, both p<0.001) and eosinophils (93% and 65% inhibition, p<0.001 and p<0.01 respectively).

Figure 9:
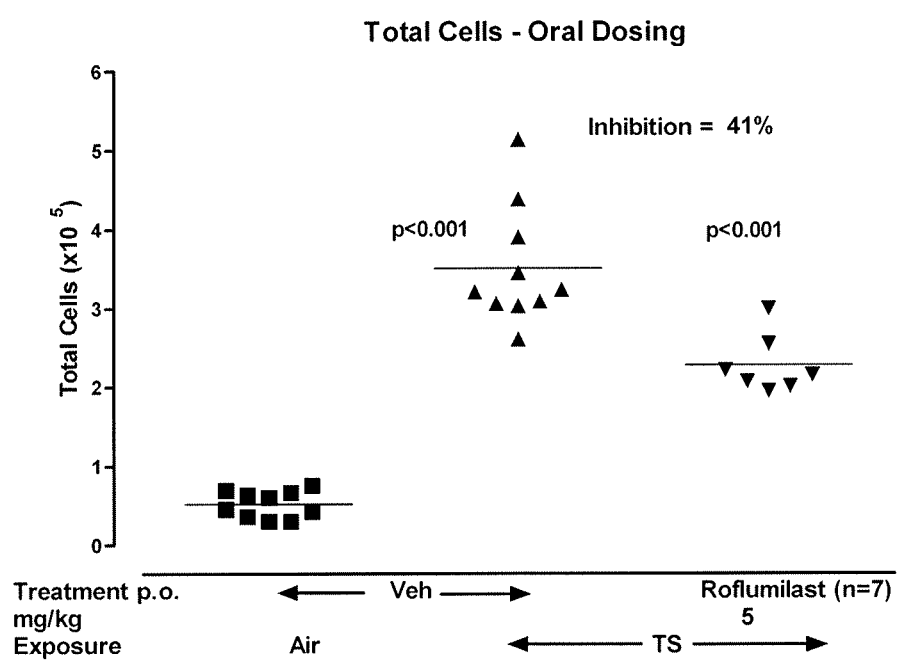
FIG. 9 illustrates reduction in total cell counts in bronchoalveolar lavage fluid from control roflumilast treated tobacco smoke exposed mice compared to vehicle treated mice.

The reference compound, Roflumilast, when given once daily orally, 1 h prior to TS exposure, also significantly reduced the total number of cells (41%, p<0.001) (FIG. 9). This inhibition was comprised of reductions in neutrophils (63% p<0.001), epithelial cells (51% p<0.01) and lymphocytes (65%, p<0.001). In this study Roflumilast did not significantly reduce the number of macrophages and eosinophils found in the BAL.

EXAMPLE 4

Effects of VAP-1 Inhibitors on Neointimal and Medial Fibrosis in the Vascular Wall Neointimal and medial thickening is an early and essential stage in the development of atherosclerotic lesions and an essential component of restenosis. It is accompanied by fibrotic changes in the neointima and media of the vascular wall. This study evaluated the role of blocking SSAO in fibrotic disease by evaluating the effect of systemic delivery (by daily ip injection) of a small molecule SSAO inhibitor (mofegiline, BTT-2089) on cuff-induced neointimal thickening (cuff-induced stenosis) in the femoral artery of ApoE3 Leiden mice that received a moderate western type diet.

Figure 10:
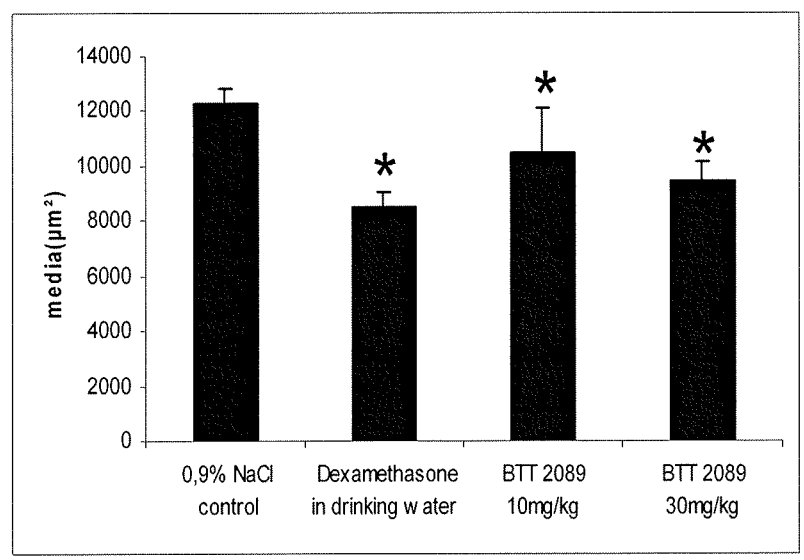
FIG. 10 shows significant reduction in media formation in the dexamethasone-treated group and both SSAO inhibitor (BTT-2089) treated groups compared to the NaCl 0.9% treated control group.
Figure 11:
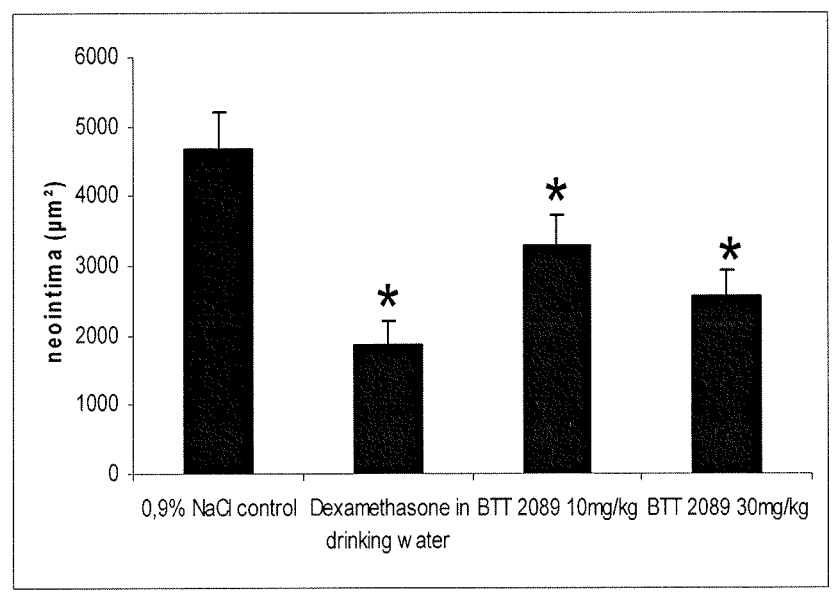
FIG. 11 shows significant reduction in neointima formation in the dexamethasone-treated group and both SSAO inhibitor (BTT-2089) treated groups compared to the NaCl 0.9% treated control group.
Figure 12:
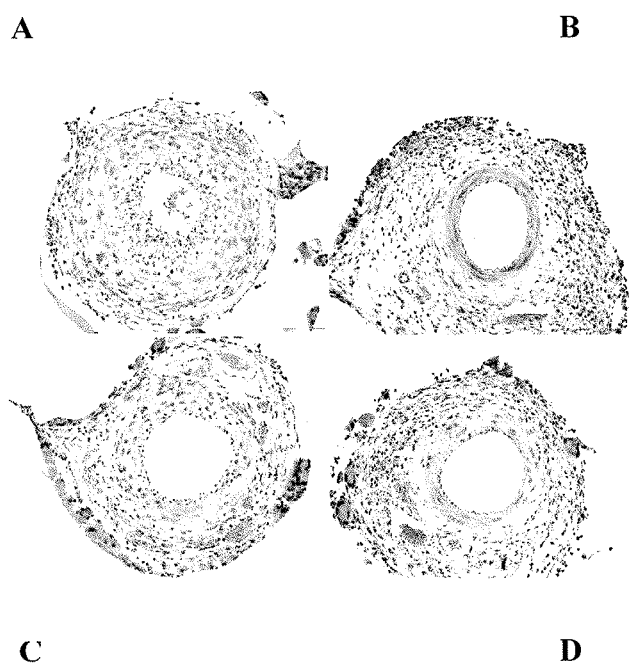
FIG. 12 shows examples of hematoxylin phloxine saffron (HPS) stained vessel segments. Lumen size is increased in SSAO inhibitor treated groups C and D when compared to control group A. A—NaCl 0.9% group; B—Dexamethasone; C—BTT2089 10 mg/kg; D—BTT-2089 30 mg/kg.

Methods: 40 male ApoE3*Leiden mice (age 12 weeks) were fed a mildly hypercholesterolemic diet for 3 weeks prior to surgical cuff placement. Treatment was daily ip injections with 1) vehicle; 2) dexamethasone in drinking water at 9 mg/I; 3) daily ip injections of BTT-2089 at 10 mg/kg; 4) BTT-2089 at 30 mg/kg, all started one day prior to surgery and continued during the experimental period. At day 0 surgery was performed, i.e. a non-constricting cuff (2-3 mm in length) was placed around both femoral arteries of the mice. 10 mice of each group were sacrificed after 2 weeks for histomorphometric analysis to quantify the inhibition of accelerated atherosclerotic lesions and neointima formation. A significant reduction in media and neointima formation in the dexamethasone-treated positive control group and both BTT-2089 treated groups compared to the NaCl 0.9% treated control group was seen (FIGS. 10 and 11). This was reflected in the increased lumen size in examples of HPS stained vessel segments in SSAO inhibitor treated groups when compared to a control group (FIG. 12).

A second study, in the same model, was performed with another SSAO inhibitor from a chemical class distinct from BTT-2089. This hydrazine based inhibitor (BTT-2079) was dosed at a level of 10 mg/kg by daily i.p injection and compared with BTT-2089 at 30 mg/kg. In all other respects the study was performed in the same manner except that the dexamethasone control group was omitted. Inhibition of SSAO with mofegiline (BTT-2089) at 30 mg/kg i.p. daily again had a beneficial effect and showed a significant reduction in neointima formation and percentage lumen stenosis after SSAO inhibition. The group treated with the SSAO inhibitor BTT-2079 10 mg/kg i.p. daily also resulted in a significant reduction in neointima formation. No significant changes between all groups were seen in vessel wall diameter, media and lumen area. The intima media ratios of the BTT-2079 10 mg/kg and BTT-2089 30 mg/kg were significantly less compared to the control group, but percentage lumen stenosis was only significantly less in the BTT-2089 30 mg/kg group compared to the control group. Vascular integrity was not affected.

These studies show that systemic dosing with SSAO inhibitors results in less neointimal thickening (neointimal fibrosis) in the ApoE 3 Leiden mice cuff model when compared with a control treated group.

EXAMPLE 5

Effects of VAP-1 Inhibitors in Mouse Model of Pulmonary Fibrosis

Bleomycin-induced lung fibrosis is an established and reproducible mouse model for studying pulmonary fibrosis.

Male C57BL/6J mice at the age of 8 weeks are treated systemically with bleomycin (100 mg/kg) for 7 days by ALZET® osmotic minipumps to elicit pulmonary damage. Non-pulmonary toxicity is observed for days 7-21 after pump implantation. By 21 days there is 12-15% fibrosis in the lungs as evaluated histopathologically. This is followed by clinical lung damage which may be observed by increased breathing rate and dramatic loss in body weight and eventually lead death within 42 days (if not terminated before).

Mice are randomly divided into study groups and treated a vehicle, VAP-1 inhibitor or reference compound by i.v. injection every third day from Day 0 to Day 28. Half of the mice of each study group are terminated on Day 21, while the other half is terminated on Day 28.

At autopsy, lungs are fixed (10% neutral buffered formalin) and subjected to histopathological processing for grading of fibrotic lesions. Tissue sections are stained with H&E and Masson's Trichrome to identify fibrosis. The ratio of fibrotic lung area to total lung area is quantified with computer-assisted image analysis for each mouse.

One-way ANOVA followed by suitable post hoc test is used for analysis of significance in samples with more than two variable groups.

A reduction in pulmonary fibrosis, as evidenced by statistically significant reductions in scoring in comparison to controls, can be shown.

EXAMPLE 6

Renoprotective Effects of VAP-1 Inhibitors in Mouse Model of Diabetic Kidney Disease Diabetes can cause diabetic nephropathy (DN) associated with progressive renal fibrosis, eventually reducing functioning renal mass. To asses the effect of anti-VAP-1 antibodies and SSAO inhibitors on renal fibrosis, a well-established Db/db diabetic mouse model for diabetic kidney disease was employed.

All aspects of these experiments (housing, experimentation and disposal of animals) were performed in general accordance with the Guide for the Care and Use of Laboratory Animals (National Academy Press, Washington, D.C., 1996).

The test article, SSAO inhibitor BTT-2079, was evaluated for possible renoprotective effect in a mouse model of diabetic nephropathy. Test substance and vehicle were administered intraperitoneally (IP) once daily for 42 consecutive days to db/db mice (BKS Cg-Lepr db/Lepr db) at the age of 15 weeks when diabetes was fully established. Db/m mice served as lean normal control. The db/db mice showed elevated plasma creatinine, signifying impaired kidney function, as well as hyperglycemia and dyslipidemia (LDL, total cholesterol and triglycerides) in comparison to db/m mice. The diabetic mice were associated with obesity, polyuria, albuminuria and increased fractional urinary $Na^+$ excretion (FENa), indicating impaired tubular $Na^+$ reabsorption. The endogenous creatinine clearance (CCr), an estimate of glomerular filtration rate, tended to be lower in the diabetic mice vs db/m mice.

Male db/db non-insulin dependent diabetic mellitus mice were assigned to treatment groups, as outlined below.

TABLE 1

Summary of experimental design

| Group | Animals | Test Article | Dosage (mg/kg) | Number of Animals (males) |
|---|---|---|---|---|
| 1 | db/m | Vehicle | 0 | 8 |
| 2 | db/db | Vehicle | 0 | 8 |
| 3 | db/db | BTT-2079 | 5 | 8 |
| 4 | db/db | BTT-2079 | 15 | 8 | db/m: non-diabetic lean heterozygotes
db/db: BKS Cg-Lepr db/Lepr db mice; non-insulin dependent diabetic mellitus
All vehicle and test article administration was by intraperitoneal injection.

At the completion of the in-life phase necropsies were performed, including collecting and preserving tissues. The right kidney from all 32 animals was fixed in 10% neutral buffered formalin. Longitudinal sections were trimmed and processed to paraffin blocks, sectioned at 3 microns and stained by periodic acid Schiff (PAS) for evaluation by light microscopy. Mesangial matrix expansion was scored in 50 glomeruli per kidney according to the semi-quantitative scoring scheme outlined in the protocol below.

Fifty glomeruli from each kidney were scored for mesangial matrix expansion according to the following system.

Minimal: grade 1, 0-25% of glomerular volume occupied by matrix

Mild: grade 2, 25-50% of glomerular volume occupied by matrix

Moderate: grade 3, 50-75% of glomerular volume occupied by matrix

Severe: grade 4, 75-100% of glomerular volume occupied by matrix

An average mesangial matrix expansion score for each group was derived by summing the mesangial matrix scores for all animals in each group and dividing the sum by the total number of animals in the group. Mean group mesangial matrix expansion scores are presented in the following table.

TABLE 2

Mean group meangial matrix espansion scores

| Group | Treatment | Mean Group Mesangial Matrix Expansion Scores |
|---|---|---|
| 1 | Vehicle | 54.6 |
| 2 | Vehicle | 96.5 |
| 5 | BTT-2079, 5 mg/kg | 82.4 |
| 6 | BTT-2079, 15 mg/kg | 65.4 |

Little glomerular mesangial matrix can be seen in normal animals but expansion of the mesangial matrix is characteristic of a variety of disease states such as diabetes mellitus. The mesangial matrix includes the basement membrane and associated polyanionic proteoglycans and other molecules which are stained red to purple by the periodic acid Schiff (PAS) method. Thus, the amount of PAS positive material in the glomerulus is a measure of the amount of mesangial matrix present.

Fifty glomeruli from each animal were evaluated at a magnification of 200× and scored for expanded mesangial matrix using the scoring system described above. Mean group mesangial matrix expansion scores were calculated by summing the scores for each glomerulus evaluated for each animal. The mesangial matrix expansion scores for all animals in the group were then summed and divided by the number of animals per group to obtain the mean group mesangial matrix expansion score. Based on these data, treatment with BTT-2079 at 5 and 15 mg/kg reduced the mesangial matrix expansion score in a dose-related manner relative to the mean group mesangial matrix expansion score in the db/db non-insulin dependent diabetes mellitus mice (Group 2).

To assess the effect of anti-VAP-1 antibodies and SSAO inhibitors on renal fibrosis other well-established mouse models for diabetic kidney disease are employed 1) Streptozotocin-induced diabetic mouse model 2) Unilateral ureteral obstruction, renal fibrosis model.

1) Streptozotocin-induced diabetic mouse model. Male mice aged 6-7 weeks (20-25 g body weight) are fasted for 6 h prior to streptozotocin (STZ) injection. To induce diabetes, freshly mixed STZ (7 mg/ml in sodium citrate buffer) is injected intraperitoneally into each pre-starved mouse at 55 mg/kg. To complete the induction of the disease, this procedure is repeated so that each mouse receives one STZ injection for five consecutive days. One week after the final STZ injection, mice with a non-fasting blood glucose of less than 280 mg/dL are excluded from the experiment as these mice will usually not develop sufficient diabetes to cause significant renal injury.

All mice are dosed with a vehicle or test substance intraperitoneally every second day for three consecutive weeks at appropriate volumes. All animals are given normal laboratory chow and water ad libitum.

Serum chemistry levels are determined by enzymatic method (Mutarotase-GOD) from blood samples. Renal injury is assessed biochemically, by measuring the urine albumin excretion and creatinine clearance, and further, histologically by Masson trichrome and Periodic acid Schiff staining.

2) Unilateral ureteral obstruction—renal fibrosis model. All mice are dosed with a vehicle or test substance intraperitoneally five days pre-operatively and 7 days post-operatively. The inhibitor and vehicle is injected every second day at an appropriate amount to inhibit SSAO. All animals are given normal laboratory chow and water ad libitum.

Male mice aged 6-7 weeks (20-25 g body weight) are anesthetised with isoflurane (2-chloro-2-(difluoromethoxy)-1, 1,1-trifluoro-ethane) inhalation and injected subcutaneously with 0.05-0.1 mg/kg buprenorphine pre-operatively. The mice are subjected to unilateral ureteral obstruction (UUO) or a sham operation. In UUO operated mice, the left ureter is ligated with a 4-0 silk suture at two points and cut between the ligatures in order to prevent retrograde urinary tract infection. The mice are sacrificed 7 days post-operatively.

Renal injury is assessed biochemically, by measuring the urine albumin excretion and creatinine clearance, and further, histologically by Masson trichrome and Periodic acid Schiff staining.

One-way ANOVA and Dunnett's tests are used in all studies to ascertain significant differences between treated and vehicle groups. Differences are considered significant at *$P<0.05$.

A reduction in renal fibrosis, as evidenced by statistically significant reductions in scoring in comparison to controls, can be shown.

EXAMPLE 7

Anti-fibrotic Therapy for Diabetic Nephropathy

Diabetic nephropathy is a common cause of end stage kidney disease and fibrosis, particularly interstitial fibrosis, is a key pathological feature of the diabetic kidney. A clinical study can determine whether inhibitors of VAP-1 can reduce nephropathy in patients with diabetes so as to prolong kidney function.

Adult patients with type 1 or 2 diabetes with a glomerular filtration rate (GFR) of between 20-75 ml/min/1.73 m2, greater than 300 mg/day of proteinuria, and blood pressure less than or equal to 140/90 on an angiotensin converting enzyme (ACE) inhibitor or an angiotensin receptor antagonist (ARA) are enrolled in a study. Patients receive a VAP-1 inhibitor at an efficacious level or a placebo for 1 year with a suitable dosing regimen which may be once daily, or less often. Patients are randomly assigned into the placebo or VAP-1 inhibitor groups. During the study patients are regularly monitored for parameters such as fasting blood and urine glucose levels, blood pressure and clinical chemistry. Additional blood samples may be drawn to measure levels of serum VAP-1 SSAO which may be elevated in diabetes and linked to the progression of the disease. In addition the levels of methylamine in the serum samples can be evaluated. Elevated methylamine is a biomarker for inhibition of VAP-1 SSAO activity. Patients are asked to regularly check their blood pressure and blood glucose at home and record the values obtained in order to monitor their diabetic state. Through insulin administration in appropriate amounts good control of the patients diabetes can be maintained in this manner.

Patients are maintained on the current standard of care for diabetic nephropathy, which can include treatment with an ACE inhibitor and/or ARA, antihypertensive therapy with a blood pressure target of less than 130/80, and tight glycemic control with appropriately set targets for HbA1C.

Renal function is assessed by the GFR and the primary endpoint of the study can be the change in renal function from baseline to the end of the study period. The secondary endpoints can include the percent change in urinary albumin excretion over the study period.

EXAMPLE 8

VAP-1 as Diagnostic Marker for Fibrotic Conditions

Figure 13:
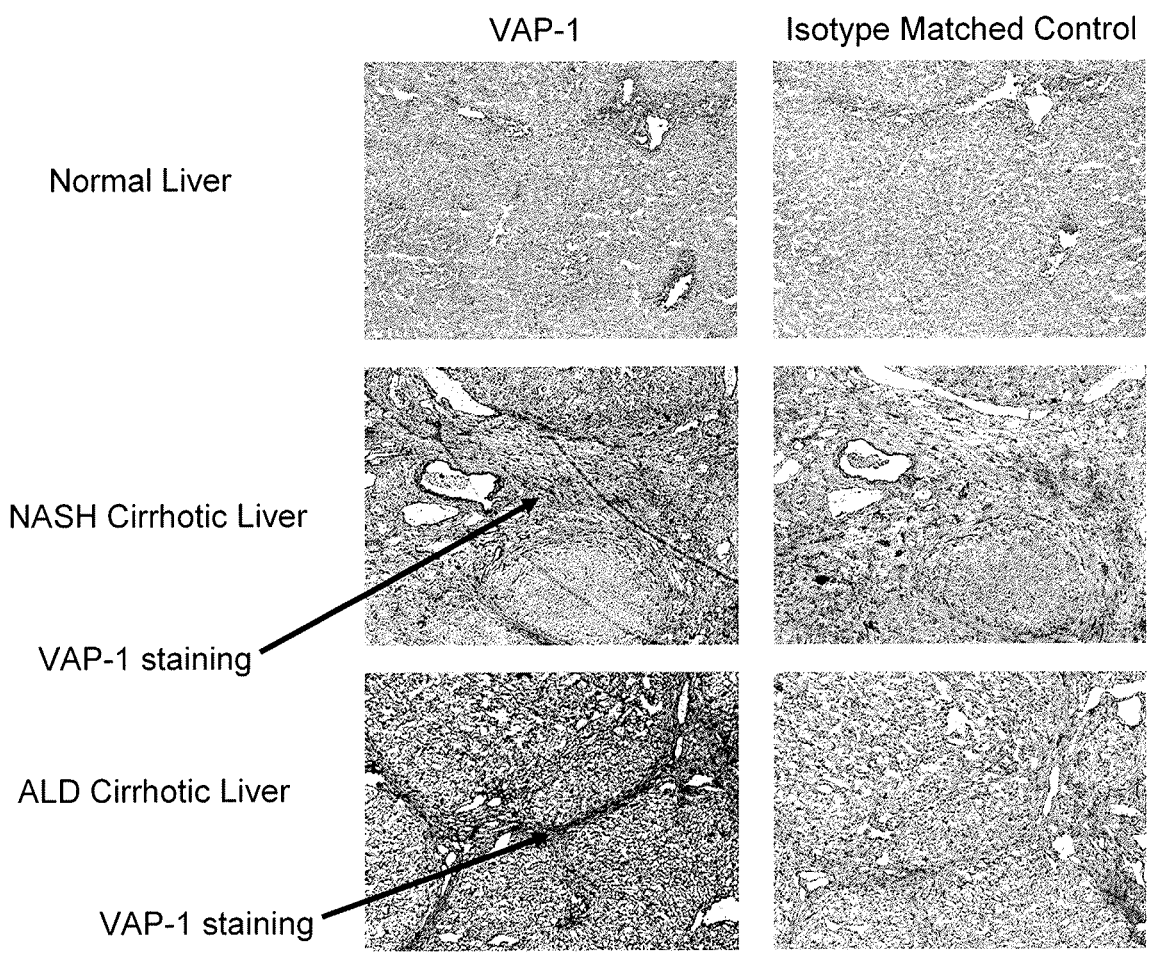
FIG. 13 shows tissue from normal, NASH cirrhotic and ALD cirrhotic liver stained with an anti-VAP-1 antibody or an isotype matched control antibody. VAP-1 staining shows darker in the NASH cirrhotic and ALD cirrhotic liver compared to normal or isotype control and reflects increase of VAP-1 expression in areas of fibrosis.
Figure 14:
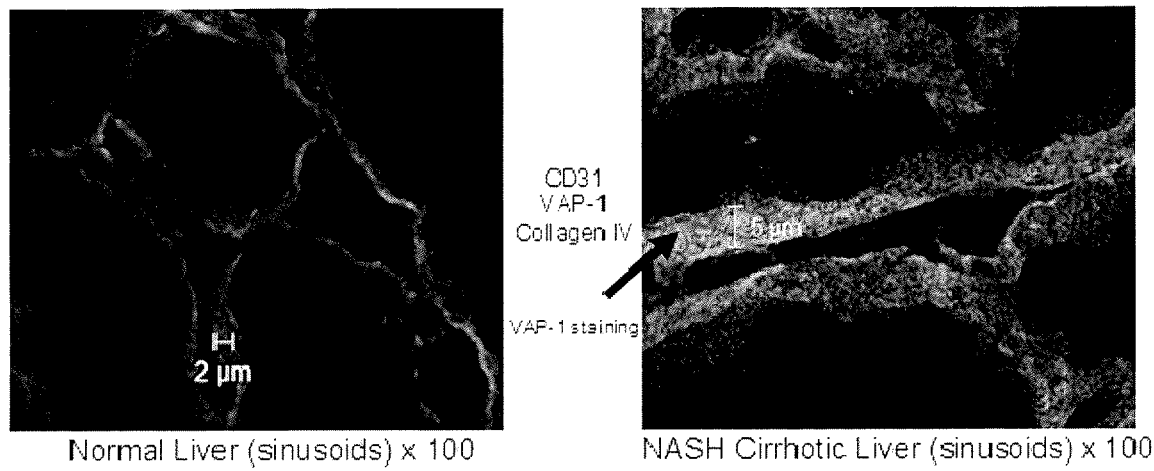
FIG. 14 shows tissue from normal and NASH cirrhotic liver stained with an anti-VAP-1, anti-CD31 and anti-collagen IV antibody. VAP-1 staining is indicated with arrows and is present predominantly only in the NASH cirrhotic liver and reflects increase of VAP-1 expression in areas of fibrosis.
Figure 15:
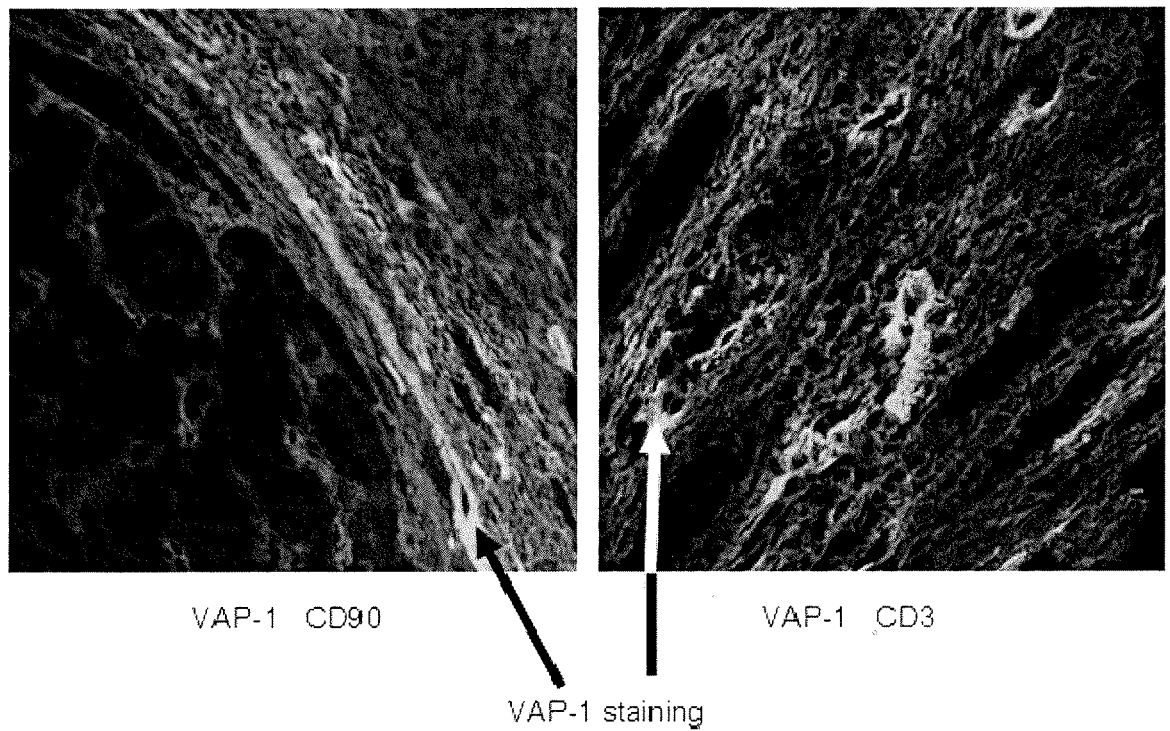
FIG. 15 shows tissue from NASH cirrhotic liver stained with an anti-VAP-1, anti-CD90 and anti-CD3 antibody. VAP-1 staining is indicated with arrows and is present in the NASH cirrhotic liver and reflects increase of VAP-1 expression in areas of fibrosis.
Figure 16:
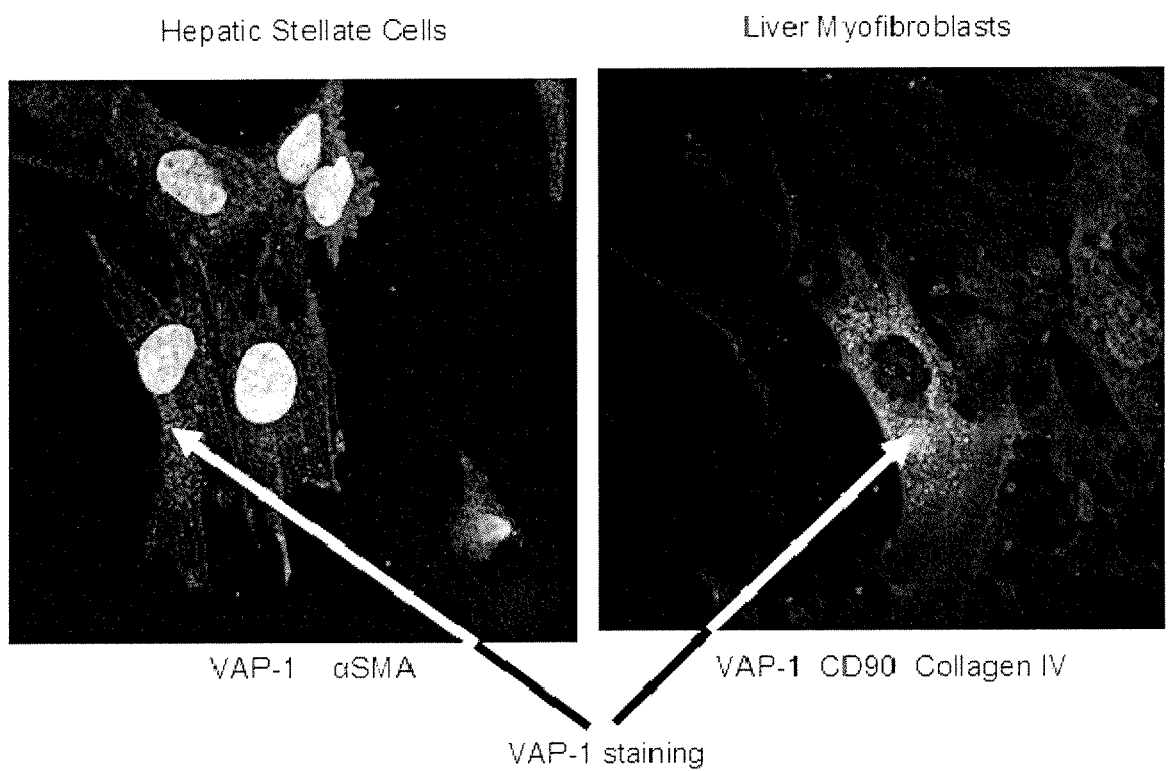
FIG. 16 shows hepatic stellate cells stained with an anti-VAP-1 and anti-smooth muscle actin antibody, and liver myofibroblasts stained with an anti-VAP-1, anti-CD90 and anti-collagen IV antibody. VAP-1 staining is indicated with arrows and is present in the hepatic stellate cells and liver myofibroblasts.

Herein, it was shown by immunohistochemistry that hepatic VAP-1 expression is increased in cirrhosis with very high levels in fibrotic septa (FIGS. 13-15). Multicolour confocal microscopy revealed VAP-1 expression on hepatic stellate cells and liver myofibroblasts (FIG. 16). Cultured human hepatic stellate cells (HSCs) were used to confirm the expression and secretion of sVAP-1 by HSCs in vitro. These results suggested a potential role for VAP-1 in fibrogenesis.

Serum sVAP-1 levels were measured in a well defined cohort of 138 patients with Non-Alcoholic Fatty Liver Disease (NAFLD) with matched and graded liver histology (Kleiner classification). sVAP-1 levels were assessed in relation to liver histology (steatosis, inflammation and fibrosis), metabolic parameters and serological markers of liver injury (Table 3).

TABLE 3

Summary of demographics and parameters measured in 138 patients with histologically graded and staged NAFLD

| VARIABLE | N = 138 |
| --- | --- |
| Age (years) | 49.4 +/− 12.2 |
| Gender (M/F) | 87(63%)/51(37%) |
| Waist Circumference (cm) | 111.4 +/− 11.5 |
| BMI (kg/m$^2$) | 35.0 +/− 5.4 |
| Normal/Overweight/Obese | 4(3%)/11(8%)/123(89%) |
| Diabetes | 61(44%) |
| HOMA-IR | 8.6 +/− 7.5 |
| Hypertension | 65(47%) |
| Total Cholesterol (mmol/l) | 5.4 +/− 1.4 |
| HDL Cholesterol (mmol/l) | 1.2 +/− 0.3 |
| Total Chol/HDL Chol | 4.7 +/− 1.6 |
| Triglycerides (mmol/l) | 2.8 +/− 2.4 |
| AST (IU/l) | 58.3 +/− 37.9 |
| ALT (IU/l) | 86.5 +/− 60.4 |
| AST/ALT Ratio | 0.80 +/− 0.47 |
| Total Bilirubin (mmol/l) | 12.3 +/− 1.6 |
| ALP (IU/l) | 105.6 +/− 52.3 |
| GGT (IU/l) | 142.8 +/− 175.1 |
| Albumin (g/l) | 44.2 +/− 4.8 |
| Platelets (x10$^9$/l) | 237.2 +/− 80.2 |
| Ferritin (ng/ml) | 198.1 +/− 471.7 |
| CRP (mg/l) | 6.0 +/− 21.6 |
| Fibrosis Stage 0/1/2/3/4 | 41/22/28/31/15 |
| sVAP-1 (ng/ml) | 945.9 +/− 457.6 |

Figure 17:
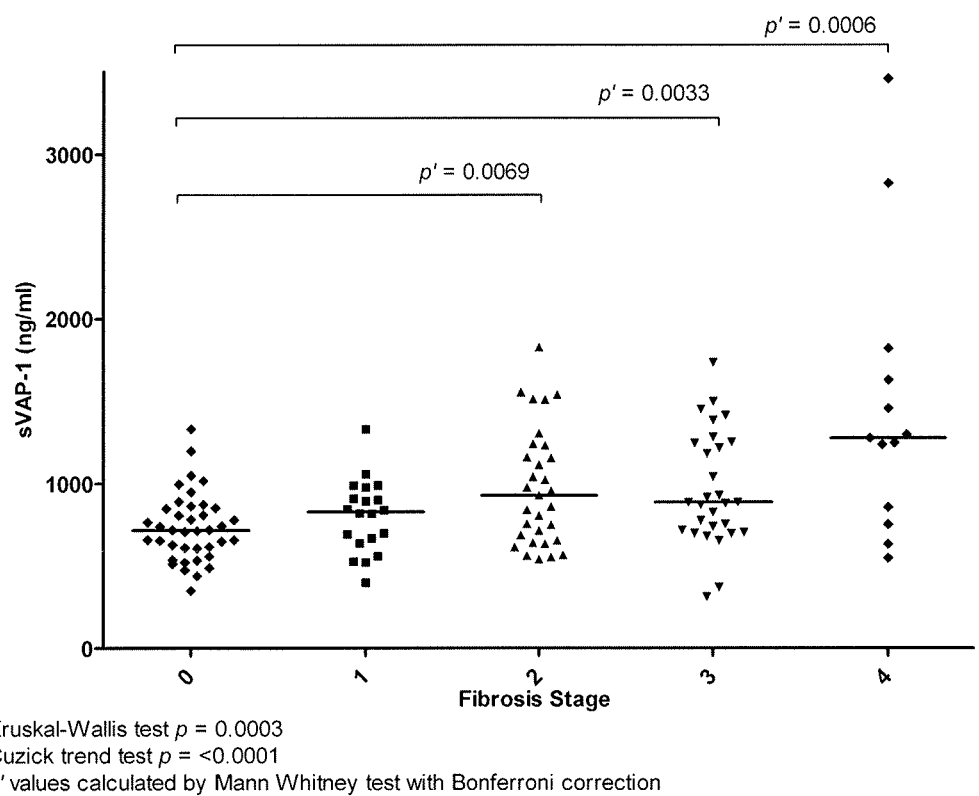
FIG. 17 is a scatter plot of sVAP-1 levels and corresponding histological fibrosis stage. Lines indicate Median values.

BMI = Body Mass Index, HOMA-IR = Homeostasis Model Assessment of Insulin Resistance, AST = Aspartate Transaminase, ALT = Alanine Transaminase, ALP = Alkaline Phosphatase, GGT = Gamma-Glutamyl Transferase, CRP = C-Reactive Protein.
sVAP-1 levels were significantly elevated in the NAFLD cohort (mean +/− SD; 945.9 +/− 457.6 ng/ml) compared with healthy individuals (300-500 ng/ml). The highest levels were seen in those with significant liver fibrosis (Stages F2-4) and there was a clear linear trend between sVAP-1 levels and fibrosis stage (FIG. 17).

Univariate correlation analysis confirmed a significant correlation between sVAP-1 levels and histological fibrosis stage (r=0.43, p=0.0000003) (Table 4) and on multiple logistic regression with backward elimination fibrosis stage was the most significant independent factor contributing to the sVAP-1 level (Table 5).

TABLE 4

Factors which correlate significantly with sVAP-1 levels on univariate analysis

| VARIABLE | r VALUE | p VALUE |
| --- | --- | --- |
| Fibrosis Stage | 0.43 | 0.0000003 |
| AST/ALT | 0.42 | 0.000002 |
| Platelets | −0.40 | 0.000002 |
| Albumin | −0.35 | 0.00003 |
| Diabetes | N/A | 0.0001 |
| Age | 0.31 | 0.0002 |
| HOMA-IR | 0.47 | 0.0003 |
| Total Bilirubin | 0.26 | 0.002 |
| ALP | 0.25 | 0.003 |
| Lobular Inflammation | 0.31 | 0.02 |
| Total Cholesterol | −0.21 | 0.02 |
| Hepatocyte Ballooning | 0.21 | 0.05 |
| Steatosis Grade | 0.18 | 0.05 | r values indicate Pearson rank correlation.

TABLE 5

Factors which are independently associated with sVAP-1 level following multiple regression with backward elimination

| VARIABLE | BETA COEFFICIENT | p VALUE |
| --- | --- | --- |
| Fibrosis Stage | 0.31 | 0.0005 |
| AST/ALT Ratio | 0.24 | 0.009 |
| ALP | 0.21 | 0.01 |
| Bilirubin | 0.20 | 0.02 |
| Steatosis Grade | 0.16 | 0.05 |

Both univariate and multivariate analysis of factors associated with significant liver fibrosis (Stages F2-4) suggested sVAP-1 levels be more significant than the standard biochemical markers of liver injury such as liver enzymes and AST/ALT ratio (Tables 6 and 7).

TABLE 6

Factors which are associated with significant fibrosis (F2-4) on univariate analysis

| VARIABLE | ODDS RATIO (95% CI) | p VALUE |
| --- | --- | --- |
| sVAP-1(continuous) | 1.003 (1.001-1.004) | 0.00006 |
| Diabetes | 4.607 (2.168-9.789) | 0.00007 |
| Age (per year) | 1.041 (1.010-1.072) | 0.008 |
| AST/ALT | 6.144 (1.525-24.756) | 0.01 |
| Hypertension | 2.628 (1.265-5.458) | 0.01 |
| Albumin | 0.913 (0.836-0.996) | 0.04 |

TABLE 7

Factors which are independently associated with fibrosis following multiple regression with backward elimination

| VARIABLE | BETA COEFFICIENT | p VALUE |
| --- | --- | --- |
| sVAP-1 | 0.32 | 0.001 |
| AST/ALT | 0.23 | 0.009 |

TABLE 7-continued

Factors which are independently associated with fibrosis
following multiple regression with backward elimination

| VARIABLE | BETA COEFFICIENT | p VALUE |
|---|---|---|
| Hypertension | 0.20 | 0.01 |
| Diabetes | 0.16 | 0.05 |

Figure 18A:
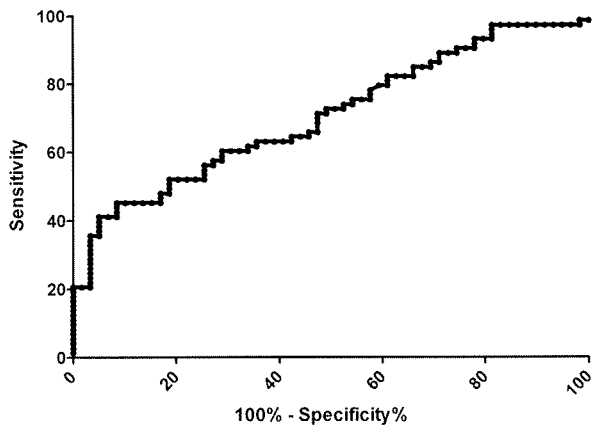
FIG. 18 shows receiver operating characteristic (ROC) curves for sVAP-1 used as a lone biomarker to predict significant liver fibrosis (F2-4) (FIG. 18A), advanced liver fibrosis (F3-4) (FIG. 18B) and cirrhosis (F4) (FIG. 18C).
Figure 18B:
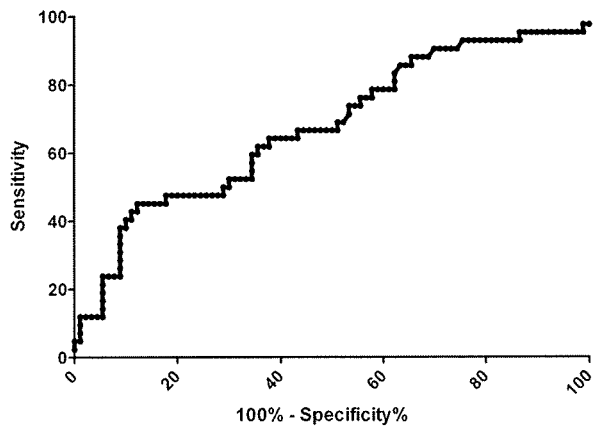
Figure 18C:
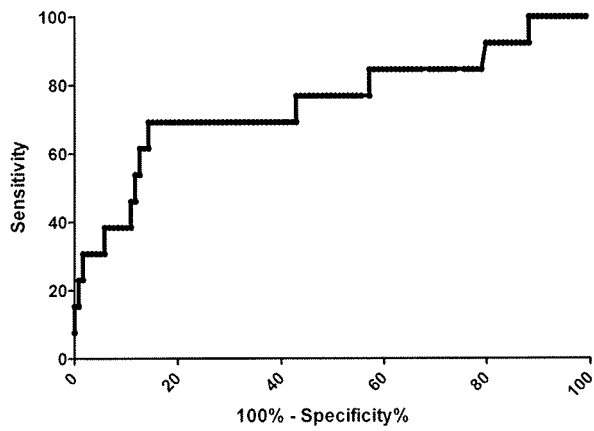

In the cohort, if the sVAP-1 level was used as a lone biomarker to predict the presence of significant liver fibrosis (Stages F2-4), a level of ≥1000 ng/ml had a positive predictive value of 88.9%. The area under the receiver operating characteristic curve (AUROC) for predicting significant fibrosis (F2-4), advanced fibrosis (F3-4) and cirrhosis (F4) was 0.71 (95% CI 0.62-0.80), 0.68 (95% CI 0.58-0.78) and 0.75 (95% CI 0.58-0.92) respectively (FIG. 18).

Figure 19A:
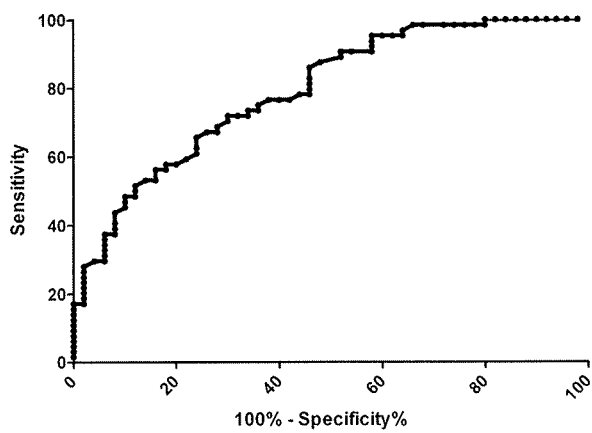
FIG. 19 shows receiver operating characteristic (ROC) curves for a fibrosis score calculated from sVAP-1 level, Diabetic status and AST/ALT ratio (0.837+sVAP-1 (ng/ml)× 0.001+Diabetes (yes=1 no=0)×0.591+logAST/ALT×0.8) to predict significant fibrosis (F2-4) (FIG. 19A), advanced fibrosis (F3-4) (FIG. 19B) and cirrhosis (F4) (FIG. 19C).
Figure 19B:
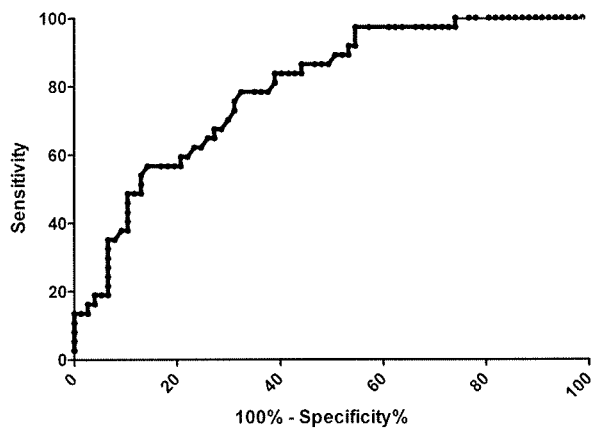
Figure 19C:
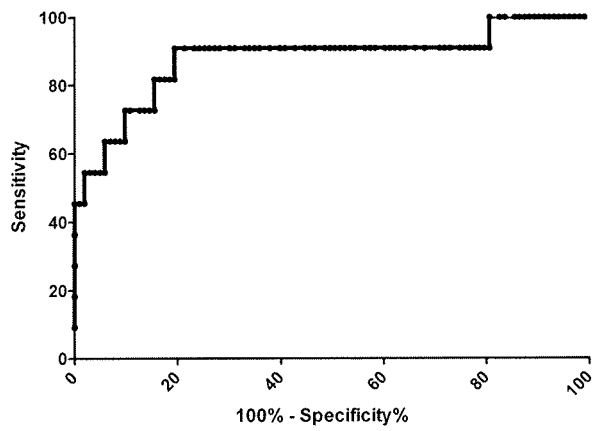

Furthermore, results suggested that there is a potential to improve upon the sensitivity and specificity profile of sVAP-1 to predict liver fibrosis by combining it with other clinical and biochemical parameters. A fibrosis score (calculated from the regression equation) of factors independently associated with liver fibrosis on multivariate analysis (sVAP-1, Diabetic status and AST/ALT ratio), had an AUROC for predicting significant fibrosis (F2-4), advanced fibrosis (F3-4) and cirrhosis (F4) of 0.79 (95% CI 0.71-0.87), 0.80 (95% CI 0.71-0.88) and 0.89 (95% CI 0.74-1.02) (FIG. 19).

The VAP-1 protein has a monoamine oxidase enzyme activity called SSAO (semicarbazide-sensitive amine oxidase). As the SSAO enzyme activity is an integral part of the VAP-1 protein it follows that levels of sVAP-1 in bodily fluids can also be determined by measuring the amount of SSAO activity in a bodily fluid (such as serum or plasma). SSAO is the principal monoamine oxidase activity in human serum and plasma acting on SSAO substrates such as benzylamine or methylamine. Thus, SSAO activity may be used as an equivalent marker of liver fibrosis.

The invention claimed is:

1. A method of alleviating a symptom of a fibrotic condition in a human subject in need thereof, said method comprising administering to said human subject an effective amount of an anti-vascular adhesion protein-1 (VAP-1) antibody wherein said antibody is a fully human recombinant antibody comprising a heavy chain polypeptide comprising CDR sequences of SEQ ID NOs: 4, 9 and 14, and a light chain polypeptide comprising CDR sequences of SEQ ID NOs: 27, 32 and 37, wherein said symptom of a fibrotic condition is selected from the group consisting of extracellular matrix accumulation associated with skin fibrosis, fibrotic lung area associated with lung fibrosis, accumulation of collagen around glomeruli or mesangial matrix expansion associated with renal nephropathy, and pulmonary inflammation associated with COPD.

2. The method according to claim 1, wherein said anti-VAP-1 antibody has a heavy chain variable region comprising an amino acid sequence as set forth in SEQ ID NO: 19, and a respective light chain variable region comprising an amino acid sequence as set forth in SEQ ID NO: 42.

3. The method according to claim 1, further comprising administering one or more additional anti-VAP-1 antibodies.

4. The method according to claim 3, wherein said one or more additional anti-VAP-1 antibodies has a heavy chain polypeptide comprising a first CDR sequence selected from SEQ ID NOs: 5 to 8, a second CDR sequence selected from SEQ ID NOs: 10 to 13, and a third CDR sequence selected from SEQ ID NOs: 15 to 18, and a light chain polypeptide comprising a first CDR sequence selected from SEQ ID NOs: 28 to 31, a second CDR sequence selected from SEQ ID NOs: 33 to 36, and a third CDR sequence selected from SEQ ID NOs: 38 to 41.

5. The method according to claim 4, wherein said additional anti-VAP-1 antibody has a heavy chain polypeptide comprising CDR sequences of SEQ ID NOs: 5, 10 and 15, and a light chain polypeptide comprising CDR sequences of SEQ ID NOs: 28, 33 and 38.

6. The method according to claim 4, wherein said additional anti-VAP-1 antibody has a heavy chain polypeptide comprising CDR sequences of SEQ ID NOs: 6, 11 and 16, and a light chain polypeptide comprising CDR sequences of SEQ ID NOs: 29, 34 and 39.

7. The method according to claim 4, wherein said additional anti-VAP-1 antibody has a heavy chain polypeptide comprising CDR sequences of SEQ ID NOs: 7, 12 and 17, and a light chain polypeptide comprising CDR sequences of SEQ ID NOs: 30, 35 and 40.

8. The method according to claim 4, wherein said additional anti-VAP-1 antibody has a heavy chain polypeptide comprising CDR sequences of SEQ ID NOs: 8, 13 and 18, and a light chain polypeptide comprising CDR sequences of SEQ ID NOs: 31, 36 and 41.

9. The method according to claim 3, wherein said additional antibody has a heavy chain variable region comprising an amino acid sequence as set forth in SEQ ID NOs: 20 to 23, and a respective light chain variable region comprising an amino acid sequence as set forth in SEQ ID NOs: 43 to 46.

10. The method according to claim 9, wherein said additional antibody has a heavy chain variable region comprising an amino acid sequence as set forth in SEQ ID NO: 20, and a respective light chain variable region comprising an amino acid sequence as set forth in SEQ ID NO: 43.

11. The method according to claim 9, wherein said additional antibody has a heavy chain variable region comprising an amino acid sequence as set forth in SEQ ID NO: 21, and a respective light chain variable region comprising an amino acid sequence as set forth in SEQ ID NO: 44.

12. The method according to claim 9, wherein said additional antibody has a heavy chain variable region comprising an amino acid sequence as set forth in SEQ ID NO: 22, and a respective light chain variable region comprising an amino acid sequence as set forth in SEQ ID NO: 45.

13. The method according to claim 9, wherein said additional antibody has a heavy chain variable region comprising an amino acid sequence as set forth in SEQ ID NO: 23, and a respective light chain variable region comprising an amino acid sequence as set forth in SEQ ID NO: 46.

14. The method according to claim 1, wherein said symptom of a fibrotic condition is extracellular matrix accumulation associated with skin fibrosis.

15. The method according to claim 1, wherein said symptom of a fibrotic condition is fibrotic lung area associated with lung fibrosis.

16. The method according to claim 1, wherein said symptom of a fibrotic condition is accumulation of collagen around glomeruli or mesangial matrix expansion associated with renal nephropathy.

17. The method according to claim 1, wherein said symptom of a fibrotic condition is pulmonary inflammation associated with COPD.

\* \* \* \* \*